US012622649B2

(12) United States Patent
Galdi

(10) Patent No.: US 12,622,649 B2
(45) Date of Patent: May 12, 2026

(54) PERSONAL HEALTHCARE DEVICE

(71) Applicant: Fabio Galdi, Santa Clara, CA (US)

(72) Inventor: Fabio Galdi, Santa Clara, CA (US)

(73) Assignee: Helo Corp., San Francisco, CA (US)

( * ) Notice: Subject to any disclaimer, the term of this patent is extended or adjusted under 35 U.S.C. 154(b) by 566 days.

(21) Appl. No.: 17/494,908

(22) Filed: Oct. 6, 2021

(65) Prior Publication Data

US 2022/0104719 A1     Apr. 7, 2022

Related U.S. Application Data

(60) Provisional application No. 63/088,223, filed on Oct. 6, 2020.

(51) Int. Cl.
*A61B 5/00*          (2006.01)
*A61B 5/02*          (2006.01)
                (Continued)

(52) U.S. Cl.
CPC .......... *A61B 5/7267* (2013.01); *A61B 5/0013* (2013.01); *A61B 5/0205* (2013.01);
                (Continued)

(58) Field of Classification Search
CPC . A61B 5/02438; A61B 5/681; A61B 5/02433; A61B 2562/0233; A61B 2562/0238; G16H 20/30
See application file for complete search history.

(56) References Cited

U.S. PATENT DOCUMENTS 6,134,458 A     10/2000  Rosenthal
2005/0159658 A1   7/2005  Jeon
            (Continued)

OTHER PUBLICATIONS

International Preliminary Report on Patentability and Written Opinion of the International Search Authority, Mar. 28, 2023 (PCT Appl. No. PCT/US2021/053549 (6 pages).

*Primary Examiner* — Oommen Jacob
(74) *Attorney, Agent, or Firm* — Nikitas E. Nicolakis; Lombard & Geliebter LLP

(57)          ABSTRACT

A wearable personal healthcare device for measuring personal health is provided that is configured to detect a photoplethysmograph (PPG) wave generated by infra-red, green, or red lights emitted from the device, the personal healthcare device. The device includes an outward facing face, a lateral side, and a bottom side, wherein the bottom side faces a user's skin, a plurality of electrical contact sensors, wherein a first of the plurality of sensors is located on one of the top face, lateral side, and bottom side, and a second of the plurality of sensors is located on one of the top face and lateral side of the personal health care device. The first and second sensors are configured to complete a circuit therebetween when a user contacts the first sensor with a first surface of the user's skin and contacts the second sensor with the first or a second surface of the user's skin. The device further includes a network communication module configured to transmit the detected PPG wave to a server, wherein the server processes the PPG wave and infers therefrom biometric data based on machine learned correlations generated from a training set of PPG waves and biometric data, a processor configured to generate the biometric data, and an interface screen comprising the biometric data.

20 Claims, 24 Drawing Sheets

(51) Int. Cl.

| | |
|---|---|
| *A61B 5/0205* | (2006.01) |
| *A61B 5/021* | (2006.01) |
| *A61B 5/024* | (2006.01) |
| *A61B 5/11* | (2006.01) |
| *A61B 5/145* | (2006.01) |
| *A61B 5/1455* | (2006.01) |
| *A61B 5/16* | (2006.01) |
| *G16H 20/30* | (2018.01) |
| *G16H 40/67* | (2018.01) |
| *G16H 50/20* | (2018.01) |
| *G16H 50/30* | (2018.01) |

(52) U.S. Cl.

CPC ...... *A61B 5/02433* (2013.01); *A61B 5/02438* (2013.01); *A61B 5/1118* (2013.01); *A61B 5/14532* (2013.01); *A61B 5/1455* (2013.01); *A61B 5/681* (2013.01); *A61B 5/7246* (2013.01); *A61B 5/7278* (2013.01); *A61B 5/742* (2013.01); *G16H 20/30* (2018.01); *G16H 40/67* (2018.01); *G16H 50/20* (2018.01); *G16H 50/30* (2018.01); *A61B 5/0002* (2013.01); *A61B 5/02* (2013.01); *A61B 5/021* (2013.01); *A61B 5/024* (2013.01); *A61B 5/165* (2013.01); *A61B 5/4815* (2013.01); *A61B 2562/0233* (2013.01); *A61B 2562/0238* (2013.01)

(56) References Cited

U.S. PATENT DOCUMENTS

| | | | |
|---|---|---|---|
| 2007/0094776 | A1 | 5/2007 | Stevens |
| 2009/0059730 | A1* | 3/2009 | Lyons .................... G04G 21/08 |
| | | | 368/69 |
| 2009/0306487 | A1* | 12/2009 | Crowe .............. A61B 5/14551 |
| | | | 600/322 |
| 2012/0057164 | A1 | 3/2012 | Tezuka |
| 2014/0142403 | A1 | 5/2014 | Brumback |
| 2015/0190063 | A1* | 7/2015 | Zakharov ............. A61B 5/1107 |
| | | | 600/479 |
| 2015/0366469 | A1* | 12/2015 | Harris .................. A61B 5/0022 |
| | | | 600/301 |
| 2016/0106941 | A1* | 4/2016 | Hickey ............. A61M 15/0086 |
| | | | 128/203.29 |
| 2016/0113526 | A1 | 4/2016 | Nageshwar |
| 2016/0124633 | A1* | 5/2016 | Kim ....................... G06F 3/0485 |
| | | | 715/773 |
| 2016/0208366 | A1 | 7/2016 | Mikaki |
| 2016/0231772 | A1* | 8/2016 | Huang ............... G06F 3/04886 |
| 2016/0242683 | A1 | 8/2016 | Ishiguro |
| 2016/0302706 | A1 | 10/2016 | Richards |
| 2017/0003720 | A1* | 1/2017 | Robinson ............. G06F 1/1632 |
| 2017/0065010 | A1 | 3/2017 | Brown |
| 2017/0079578 | A1 | 3/2017 | van den Broek |
| 2017/0156676 | A1 | 6/2017 | Ferber et al. |
| 2018/0129334 | A1* | 5/2018 | Bostick ............... G06F 3/04817 |
| 2018/0181733 | A1* | 6/2018 | Shim ....................... G06F 21/32 |
| 2018/0217682 | A1* | 8/2018 | Dangy Caye .......... G04G 21/08 |
| 2018/0353137 | A1* | 12/2018 | Balajadia .............. A61B 5/681 |
| 2021/0228159 | A1 | 7/2021 | Galdi |
| 2022/0104719 | A1* | 4/2022 | Galdi .................... G16H 20/30 |

\* cited by examiner

1.LED

| LED Spec | | Wavelength | Attributes | Name |
|---|---|---|---|---|
| | LED2 | 940nm | Infrared | LED640 |
| | | | | LED940 |
| | LED3 | 1300nm | Infrared | LED1300 |
| | LED4 | 1550nm | Infrared | LED1550 |

| LED Function | | Monitoring project | LED combination |
|---|---|---|---|
| | | Heart rate | LED640 * LED940 * LED1300 * LED1550 |
| | | Blood oxygen | LED640 + LED940 |
| | | blood sugar | LED640 + LED940 + LED1300 + LED1550 |

FIG. 6B

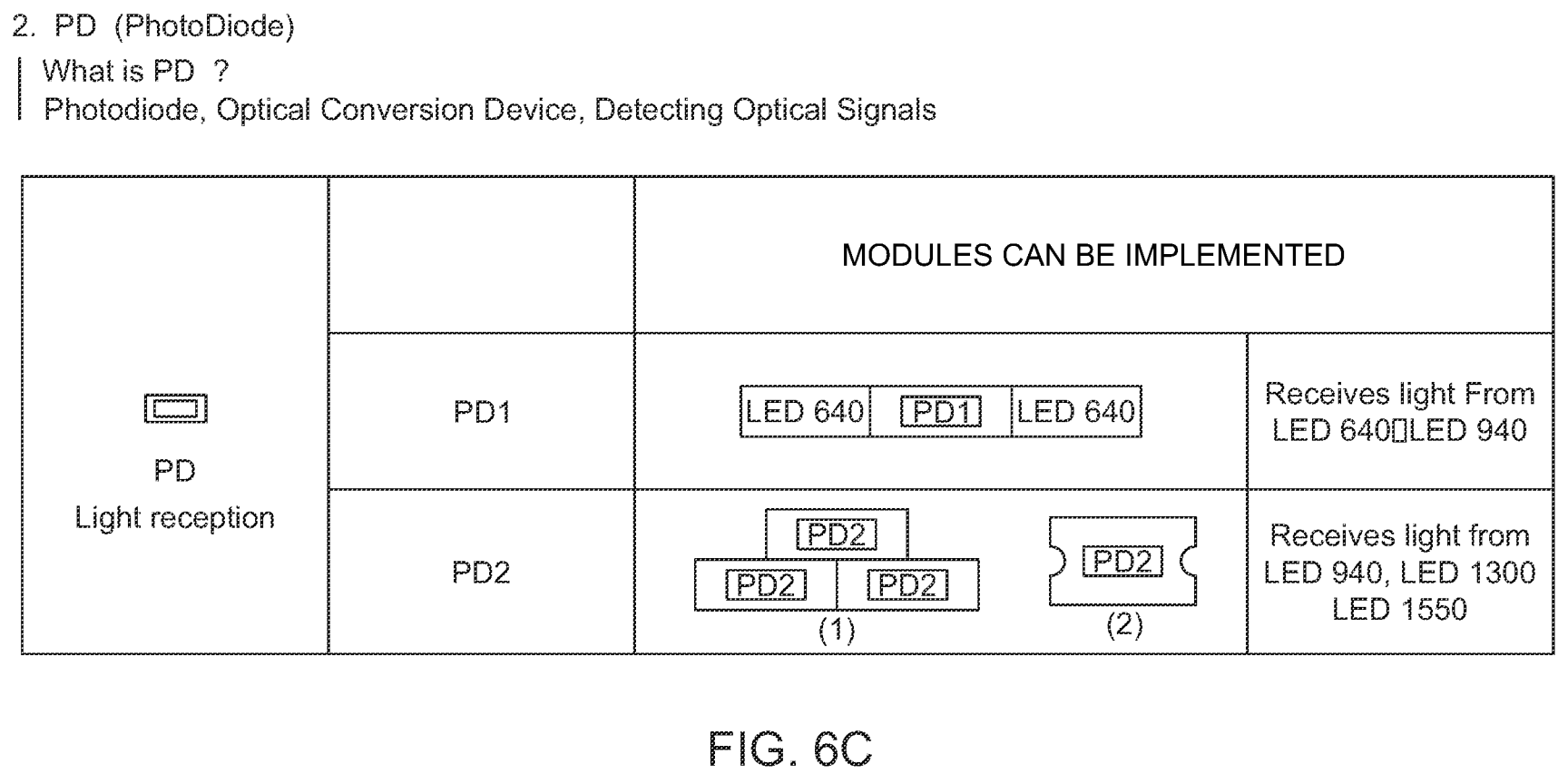

2. PD (PhotoDiode)
What is PD ?
Photodiode, Optical Conversion Device, Detecting Optical Signals

| | | MODULES CAN BE IMPLEMENTED | |
|---|---|---|---|
| ☐ PD | PD1 | LED 640 PD1 LED 640 | Receives light From LED 640☐LED 940 |
| Light reception | PD2 | PD2 PD2 PD2 (1)    PD2 (2) | Receives light from LED 940, LED 1300 LED 1550 |

FIG. 6C

PERSONAL HEALTHCARE DEVICE

RELATED APPLICATION

This application claims the benefit of U.S. Provisional Patent Application No. 63/088,223, filed on Oct. 6, 2020, which is hereby incorporated herein by reference.

BACKGROUND OF THE INVENTION

The present application relates to wearable healthcare devices and more particularly devices that gather data and monitor a user's biometrics.

One of the challenges when using photoplethysmogram (PPG) technology in smartwatches and other wearable devices is pulse signal detection difficulty because of scattering of reflected light due to the device location. In the case of smartwatches and other wristband devices, Light Emitting Diodes (LEDs) and Photodiodes (PDs) are typically positioned on the wrist where a relatively high presence of bones and low levels of capillaries and veins, and an inadequate skin-sensor seal, cause poor reflection of the various wavelengths of light used in pulse signal detection. This is particularly problematic when high frequency wavelength light is used for pulse signal detection, and it results in weak DC and AC signals, yielding high signal-to-noise ratios and poor quality PPG signals.

In medical and clinical applications, this problem of detecting the pulse signal is addressed with the use of a fingertip sensor. The fingertip is an area of the body where there is almost no bone, a wide presence of capillaries, and the opportunity for light to pass directly from the LED through the skin to the PD and where the skin can form a better seal with the LED and PD, resulting in more uniform light scattering effects and more accurate and efficient detection of the pulse wave.

A fingertip oximeter is an example of such a device. Typically, a cabled or wireless clip is attached to the finger and LEDs emit Infrared (IR) and Near Infrared (NIR) light with wavelengths between 640 nm and 940 nm. The reflected light is used to accurately detect the pulse wave, create the PPG signal from which the RR-interval (the interval between two successive heartbeats) and other important parameters can be deduced, such as Blood Oxygenation (SpO2), Heart Rate (HR), Heart Rate Variability (HRV) and Blood Pressure (BP). When other higher frequency NIR wavelengths are used, it is also possible to estimate hemoglobin and glucose levels. However, it is difficult to consider that such an attachable fingertip device is a wearable device because of its physical configuration and the need to re-attach it to the body each and every time a measurement is required. In addition, if frequent or even continuous measurements are required, then the current devices restrict the wearer's movements and it is not convenient in terms of daily or continue usage.

PPG technology is well established for fingertip use (where it can capture high quality readings because there is no bone and the fingertip skin forms a good seal with the sensor). In addition to traditional devices such as pulse oximeters that capture PPG from fingertip insertion, there are standalone devices that also capture high quality PPG signals from the fingertip, such as smartphones. However, PPG technology does not appear to have been incorporated on the side of a wrist worn device. Though side sensors on smart watches exist, no devices with IR and NIR sensors incorporated into the side of a wearable device to allow the wearer to place their fingertip on the side sensor to obtain high quality PPG readings exists. Accordingly, there is a need for a wearable device that is not so limited.

Additionally, although wearable biometric monitors are available, most have limited functionality. For instance, most are limited to measuring steps taken/distance covered and heart rate. Those interested in a more in-depth profile and understanding of their health must do so with an inconvenient trip to their health care professional which often includes an invasive procedure. Moreover, the reliability of data generated when the device is moving, is questionable and PPG signals can create measurement artifacts. Accordingly, there is a need for a wearable device with multiple sensors, detects movement and that continuously or on demand, provides high quality PPG data conveniently and without the need for invasive procedures.

1. Summary of the Invention

The present application provides method(s), wearable device(s), and computer readable media for measuring personal health. According to one embodiment, the method includes detecting a photoplethysmograph (PPG) signal by a sensor, the PPG signals are generated by infra-red, green and/or red lights emitted from one or more emitters of a personal healthcare device, transmitting the PPG signal data to a server, the server processing the PPG signal data to infer biometric statistics based on machine learned correlations generated from a training set of PPG signals and biometric data, receiving the biometric statistics from the server, and generating display data based on the biometric statistics.

The biometric statistics may include at least one of overall health, changes in health, mood, sleep quality, fatigue, and stress. The biometric data includes at least one of heart rate, respiratory rate, steps taken, calories burned, distance covered, sleep quality, ECG/EKG, blood pressure, mood, fatigue, body temperature, glucose levels, blood alcohol, and blood oxygen. In one embodiment, the machine learned correlations are based on PPG character vectors including a Kaiser-Teager power energy value, a heart rate value, and a spectral entropy value.

According to one embodiment, the wearable device includes at least one emitter configured to generate a combination of at least two of infra-red, red, and green lights, a sensor configured to detect a photoplethysmograph (PPG) signal based on the combination of lights generated from at least one emitter, a network communication module configured to transmit the PPG signal to a server and receive biometric statistics from the server, the server processing the PPG signal to infer biometric statistics based on machine learned correlations generated from a training set of PPG signals and biometric data, a processor configured to generate display data based on the biometric statistics, and a display configured to display the display data.

The wearable device may further include a wrist band including a plurality of apertures that are equally spaced to accommodate pedestals having stones thereon. A cross section of the apertures may be hourglass-shaped to retain similarly shaped legs on the pedestals. The pedestals can be inserted from the inside of the wrist band through the apertures therein. A pair of legs of the pedestals may fit flush with the outside of the wrist band. In one embodiment, the top of the pedestals includes therein at least one of gold, silver, copper, germanium, magnets, and salt. In another embodiment, the top of the pedestals includes a stone.

The biometric statistics may include at least one of overall health, changes in health, mood, sleep quality, fatigue, and stress. The biometric data may include at least one of heart rate, respiratory rate, steps taken, calories burned, distance covered, sleep quality, ECG/EKG, blood pressure, mood, fatigue, body temperature, glucose levels, blood alcohol, and blood oxygen. The machine learned correlations may be based on PPG character vectors including a Kaiser-Teager power energy value, heart rate value, and spectral entropy value.

The wearable device may further include a flat inline sensor (FIS) including a Near Field Infrared (NIR) Light Emitting Diode (LED) with signal length of approximately 1300 nanometer (nm), a NIR LED with signal length of approximately 1550 nm and a photodiode with wavelength sensitivity range between 900 nm to 1700 nm. The light from the NIR LEDs may be directed to skin via two angular mirrors such that the light is reflected back off of blood glucose molecules to the photodiode at a predetermined angle.

According to one embodiment, the non-transitory computer-readable media includes computer program code for detecting a photoplethysmograph (PPG) signal by a sensor, the PPG signals are generated by infra-red, green or red lights emitted from one or more emitters of a personal healthcare device, computer program code for transmitting the PPG signal to a server, the server processing the PPG signal to infer biometric statistics based on machine learned correlations generated from a training set of PPG signals and biometric data, computer program code for receiving the biometric statistics from the server, and computer program code for generating display data based on the biometric statistics.

The biometric statistics may include at least one of overall health, changes in health, mood, sleep quality, fatigue, and stress. The biometric data may include at least one of heart rate, respiratory rate, steps taken, calories burned, distance covered, sleep quality, ECG/EKG, blood pressure, mood, fatigue, body temperature, glucose levels, blood alcohol, and blood oxygen. In one embodiment, the machine learned correlations are based on PPG character vectors including a Kaiser-Teager power energy value, a heart rate value, and a spectral entropy value.

In another aspect, method is provided that, in a data processing system comprising a processor and a memory, for measuring personal health, includes detecting a photoplethysmograph (PPG) wave by a personal healthcare device, the PPG waves are generated by infra-red, green, or red lights emitted from the personal healthcare device; transmitting the detected PPG wave to a server, wherein the server processes the PPG wave and infers therefrom biometric data based on machine learned correlations generated from a training set of PPG waves and biometric data; receiving the biometric data from the server; and generating an interface screen comprising the biometric data. The personal health care device preferably includes: a top outward facing face, a lateral side, and a bottom side, wherein the bottom side faces a user's skin; and a plurality of electrical contact sensors, wherein a first of the plurality of sensors is located on one of the top face, lateral side, and bottom side, and a second of the plurality of sensors is located on one of the top face and lateral side of the personal health care device, wherein the first and second sensors are configured to complete a circuit therebetween when a user contacts the first sensor with a first surface of the user's skin and contacts the second sensor with the first or a second surface of the user's skin In one embodiment, the personal health care device further includes: an inline sensor (IS) comprising a first Near Field Infrared (NIR) Light Emitting Diode (LED), a second NIR LED, and a photodiode with wavelength sensitivity range between about 900 nm to about 1700 nm±10%, the photodiode located on the IS between the first and second NIR LEDs and configured relative thereto to receive reflected light from the first and second NIR LEDs, and a first and second angular mirror, each configured to reflect light from either of the first and second NIR LEDs onto a user's skin and for the user's skin to reflect light back to the photodiode, wherein the personal healthcare device generates the detected PPG wave based on the light reflected off of the user's skin.

In one embodiment, the first NIR LED has a first wavelength in the near infrared spectrum and the second NIR LED has a second wavelength in the near infrared spectrum.

In one embodiment, a first intermediate detected PPG wave is generated from light reflected off of the user's skin from the first NIR LED and a second intermediate detected PPG wave is generated from light reflected off of the user's skin from the second NIR LED, and the detected PPG wave is generated from the combination of the first and second intermediate detected PPG waves.

In one embodiment, the first NIR LED has a wavelength of about 1550 nm±10% and the second NIR LED has a wavelength of about 1300 nm±10%.

In one embodiment, light from the first NIR LED is directed to the user's skin via the first angular mirror, and light from the second NIR LED is directed to the user's skin via the second angular mirror, such that the light from the first NIR LED is reflected back off of blood glucose molecules to the photodiode at a first predetermined angle and light from the second NIR LED is reflected back off of blood glucose molecules to the photodiode at a second predetermined angle.

In one embodiment, the first predetermined angle is about 45 degrees and the second predetermined angle is about 90 degrees.

In one embodiment, at least one of the plurality of sensors is recessed within a ridge extending outward from a face or side of the device and around the perimeter of the sensor, wherein the ridge is configured to form a seal with the first or second surface of the user's skin when the user contacts the at least one of the plurality of sensors with the first or second surface of the user's skin.

In one embodiment, the plurality of sensors are covered with a glass configured to direct light from either of the first and second NIR LEDs onto a user's skin and receive reflected light from the first and second NIR LEDs at the photodiode.

In one embodiment, the inline sensor further comprises a PCB, and the first and second NIR LEDs, photodiode, and first and second angular mirrors are each attached to the PCB.

In one embodiment, the first and second NIR LEDs are configured to emit light in a direction parallel to the PCB, and wherein the mirrors reflect the emitted light at an oblique angle relative to the PCB.

In one embodiment, the biometric data comprises blood glucose levels.

In one embodiment, the server processes the PPG wave and infers therefrom biometric statistics and wherein the biometric statistics comprise at least one of overall health, changes in health, mood, sleep quality, fatigue, and stress.

In one embodiment, the machine learned correlations are based on PPG character vectors including a Kaiser-Teager power energy value, a heart rate value, and a spectral entropy value.

In another aspect, a wearable device for measuring personal health is provided that is configured to detect a photoplethysmograph (PPG) wave generated by infra-red, green, or red lights emitted from the personal healthcare device, the wearable personal health care device includes: a top outward facing face, a lateral side, and a bottom side, wherein the bottom side faces a user's skin; a plurality of electrical contact sensors, wherein a first of the plurality of sensors is located on one of the top face, lateral side, and bottom side, and a second of the plurality of sensors is located on one of the top face and lateral side of the personal health care device, wherein the first and second sensors are configured to complete a circuit therebetween when a user contacts the first sensor with a first surface of the user's skin and contacts the second sensor with the first or a second surface of the user's skin; a network communication module configured to transmit the detected PPG wave to a server, wherein the server processes the PPG wave and infers therefrom biometric data based on machine learned correlations generated from a training set of PPG waves and biometric data; a processor configured to generate the biometric data; and an interface screen comprising the biometric data.

In one embodiment, the personal health care device further comprises: an inline sensor (IS) comprising a first Near Field Infrared (NIR) Light Emitting Diode (LED), a second NIR LED, and a photodiode with wavelength sensitivity range between about 900 nm to 1700 nm±10%, the photodiode located on the IS between the first and second NIR LEDs and configured relative thereto to receive reflected light from the first and second NIR LEDs; and 2. a first and second angular mirror, each configured to reflect light from either of the first and second NIR LEDs onto a user's skin and for the user's skin to reflect light back to the photodiode, wherein the personal healthcare device generates the detected PPG wave based on the light reflected off of the user's skin.

In one embodiment, at least one of the plurality of sensors is recessed within a ridge extending outward from a face or side of the device and around the perimeter of the sensor, wherein the ridge is configured to form a seal with the first or second surface of the user's skin when the user contacts the at least one of the plurality of sensors with the first or second surface of the user's skin.

In one embodiment, the plurality of sensors are covered with a glass configured to direct light from either of the first and second NIR LEDs onto a user's skin and receive reflected light from the first and second NIR LEDs at the photodiode.

In one embodiment, the server processes the PPG wave and infers therefrom biometric statistics and wherein the biometric statistics comprise at least one of overall health, changes in health, mood, sleep quality, fatigue, and stress.

In one embodiment, the machine learned correlations are based on PPG character vectors including a Kaiser-Teager power energy value, heart rate value, and spectral entropy value.

According to one embodiment, one or more of the emitters and/or sensors are located on a side of the wearable device.

BRIEF DESCRIPTION OF THE FIGURES

FIG. 6B is a chart of details for exemplary LEDs that may be used in a preferred embodiment of the FIS according to one embodiment herein.

FIG. 6C is a chart of details of exemplary photodiodes and photodiode combinations that may be used in a preferred embodiment of the FIS according to one embodiment herein.

DETAILED DESCRIPTION OF THE INVENTION

Figure 1:
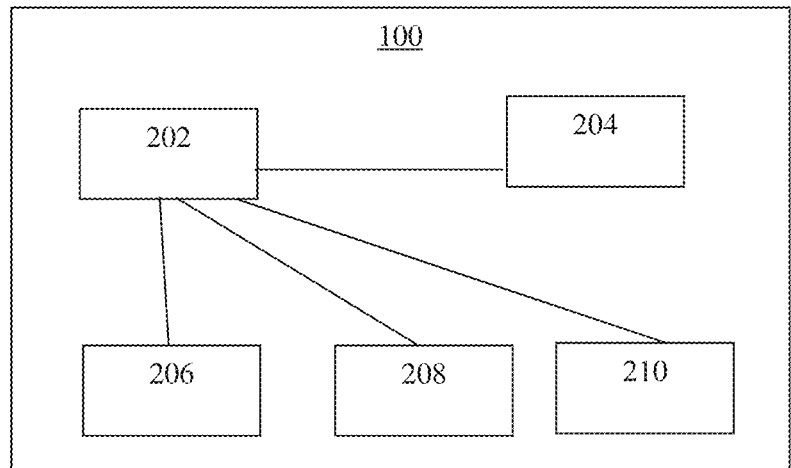
FIG. 1 is a block diagram of a personal healthcare device according to at least one embodiment herein.

Referring to FIG. 1, a wearable personal healthcare device 100 according to at least one embodiment includes a processor 202 coupled to a computer memory 204. The device 100 may be a smartwatch, smart band or other wearable electronic device. Although the device 100 may be shown and described as a watch, it is understood that the functionality may be implemented in other devices, including a smartphone or tablet, or any other device capable of performing the functionality disclosed herein, and the meaning of a device as used herein is therefore not limited thereto. The memory stores therein software that when executed causes the device 100 to perform the functions discussed herein. The processor 202 is preferably further coupled to a transmitter/receiver 206 that enables communication between the device 100 and other devices as discussed below. The device 100 preferably includes at least one emitter 208 and one or more sensors 210. The emitter 208 is generally a device that emits energy that is received by sensor 210 in a transformed state. The emitter 208 and sensor 210 are controlled by the processor 202 to emit energy and process the transformed energy, received by the sensor 210 into usable biometric data, as discussed herein. One or more sensors [and emitters] may include a sensor package that is directly connected to the main board of the device for acquisition and processing of signals. Various types of emitters may be used with the device 100, including light (visible and invisible spectrum), heat, sound, conduction, etc.

Figure 4A:
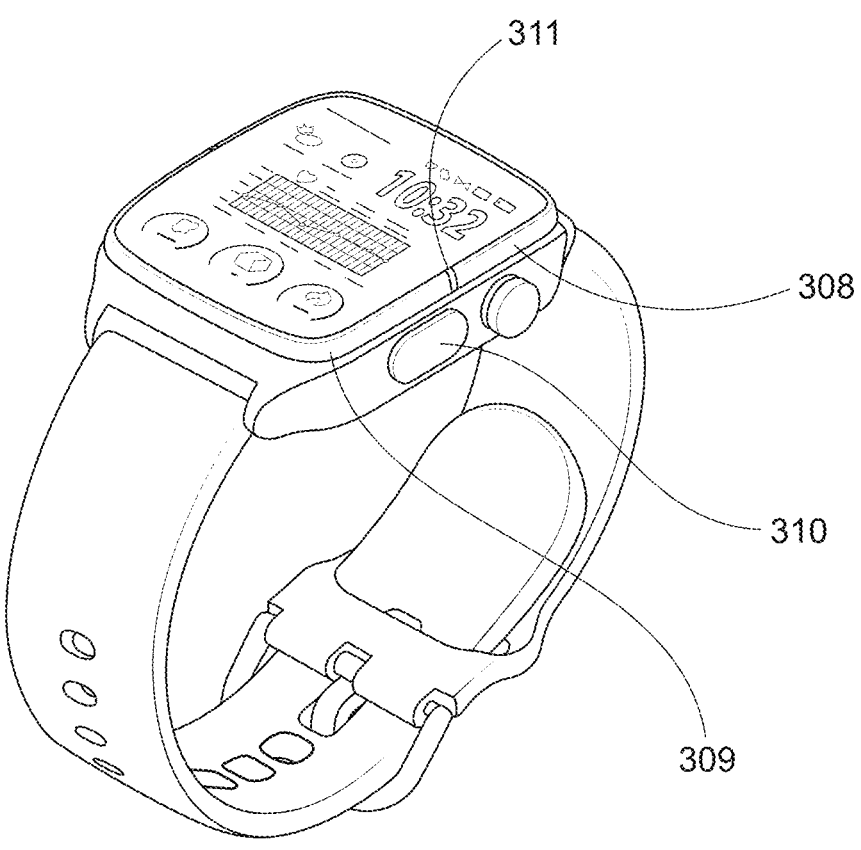
FIG. 4A is a perspective view of a personal healthcare device according to another embodiment herein.
Figure 4B:
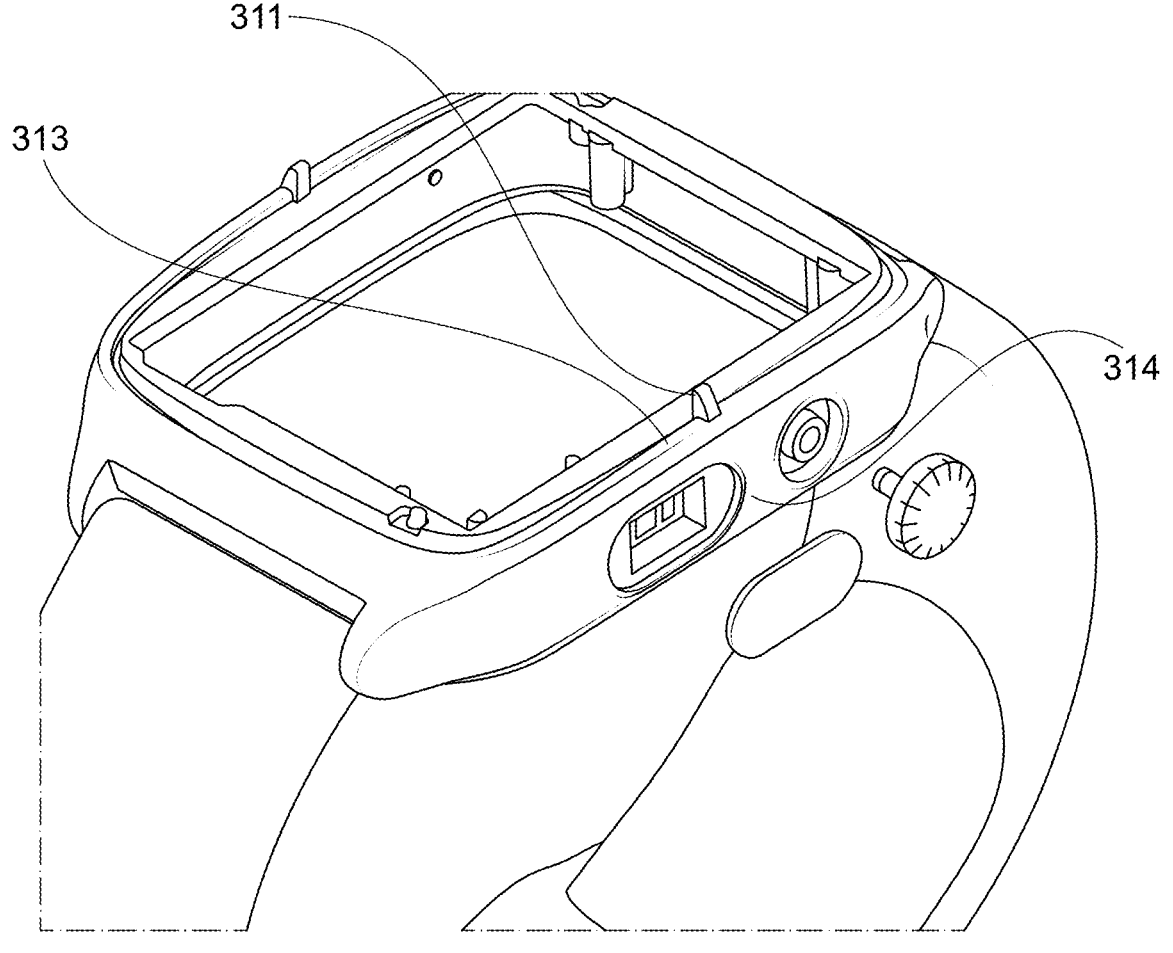
FIG. 4B is a diagram of a personal healthcare device according to another embodiment herein.

The device 100 may include a plurality of each of the emitters/sensors, such as a combination of infra-red and red lights, and corresponding sensors. The device may further include one or more sensors 210 operable to gather hemodynamic and other data which device 100 uses signal processing in processor 202 and/or other improvements to reduce the signal noise and then this data is transmitted for further processing remotely into more meaningful parameters such as heart rate, respiratory rate, fat percentage, steps taken, ECG/EKG, blood pressure, body temperature, glucose levels, blood alcohol, blood oxygen, etc. The noise may be reduced mechanically, with a raised edge on the border of the sensor glass (as shown in FIGS. 4A-4B) to provide a better seal between the LED, PD, and the fingertip. Additionally, the device may detect ambient light (e.g., with a separate sensor) at the time of the reading and erase or otherwise cancel interference or noise attributable to the ambient light. The raw data collected by the device from these sensors 210 may be processed and/or collected remotely on a server to infer, for example, overall health, changes in health, mood, sleep quality, fatigue or stress, etc.

The device 100 is therefore operable to collect data to enable a wealth of personal health data that includes one or more of the following: heart rate, respiratory rate, steps taken, calories burned, distance covered, sleep quality, ECG/EKG, blood pressure, mood, fatigue, body temperature, glucose levels, blood alcohol, blood oxygen, etc. The device 100 may also include one or more of the following features: iPhone/Android connectability, or as a standalone IoT (internet of things) device to allow for remote monitoring of vitals, for example, by a health professional, panic button (that plays audio and visual alarm, communicates GPS position and message to preconfigured address, etc.), accommodate germanium stones, provide a mosquito shield, display location based air quality, detect noxious gasses, etc.

In one embodiment, the device 100 may automatically measure certain biometric data through an internal timer. The rate at which measurements are taken may be preset or set remotely by the wearer, carer or an authorized third party. For example, the rate may be every 30 min, 60 min, etc., selected from a drop-down menu of available rates. The device 100 may further collect data continually, for use, for example, for inferring some of the conclusions therefrom while still displaying and charting the periodic measurements. For example, the device 100 may collect heart rate data continuously and use that to determine heart rate variability, while still only charting hourly measurements. In another embodiment, the device 100 may further or alternatively include sensors that assess biometric data on demand, i.e., when a user elects to take a measurement.

Figure 2:
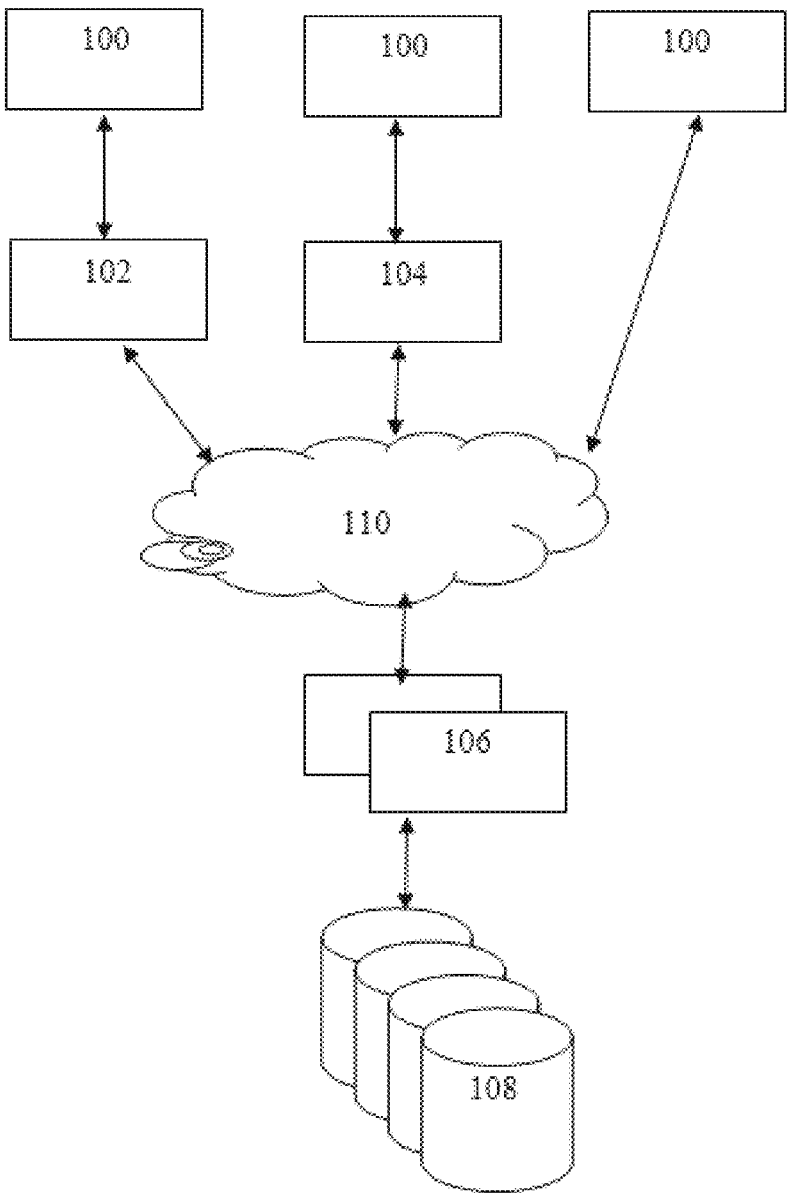
FIG. 2 is a block diagram of a personal healthcare device operating in a network environment according to at least one embodiment herein.

Referring to FIG. 2, the personal healthcare device 100 is preferably operable to communicate with other devices in a network environment. For instance, device 100 may communicate directly with a mobile device 102 (such as a phone or tablet) or a personal computer 104 via a short-range wireless connection, such as Bluetooth® or via "Internet of things" (IoT). Additionally, the device 100 may be operable to communicate indirectly with these as well as other devices over a wireless LAN or via a GSM or LTE connection. Finally, the device 100 may operate to provide the functionality discussed herein in conjunction with one or more server computers 106 that are further coupled to one or more databases 108 via the Internet 110.

In at least one embodiment, the device 100 communicates with a mobile device 102 or personal computer 104 that executes an application, which manages the results of the information received from the device 100. The application, for instance, may show current biometric data as well as historic biometric data (collected over time), as shown in FIGS. 6-11. The data may be stored locally on the mobile device 102, personal computer 104, or preferably remotely on the "cloud." With the latter, users can access the data online via a browser application. In another embodiment, the biometric data may be accessed on device 100.

Figure 3A:
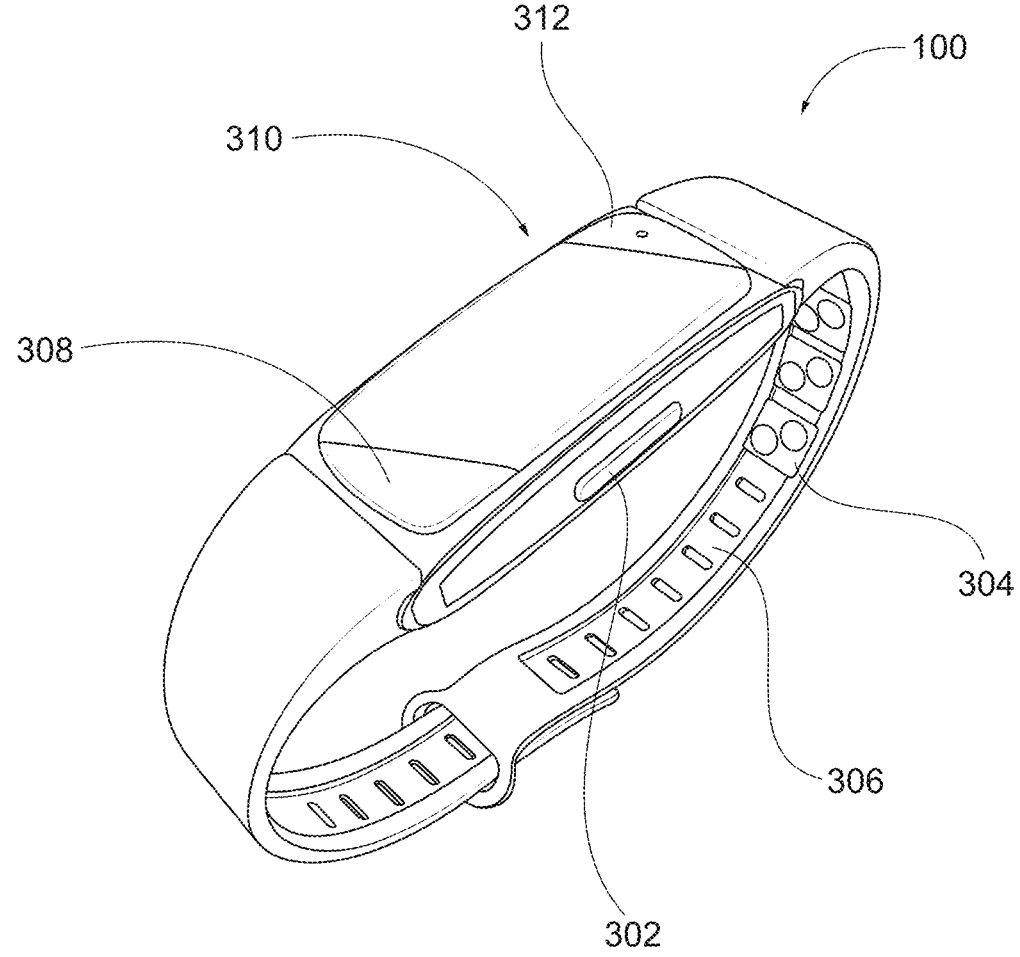
FIG. 3A is a perspective view of a personal healthcare device according to one embodiment herein.
Figure 3B:
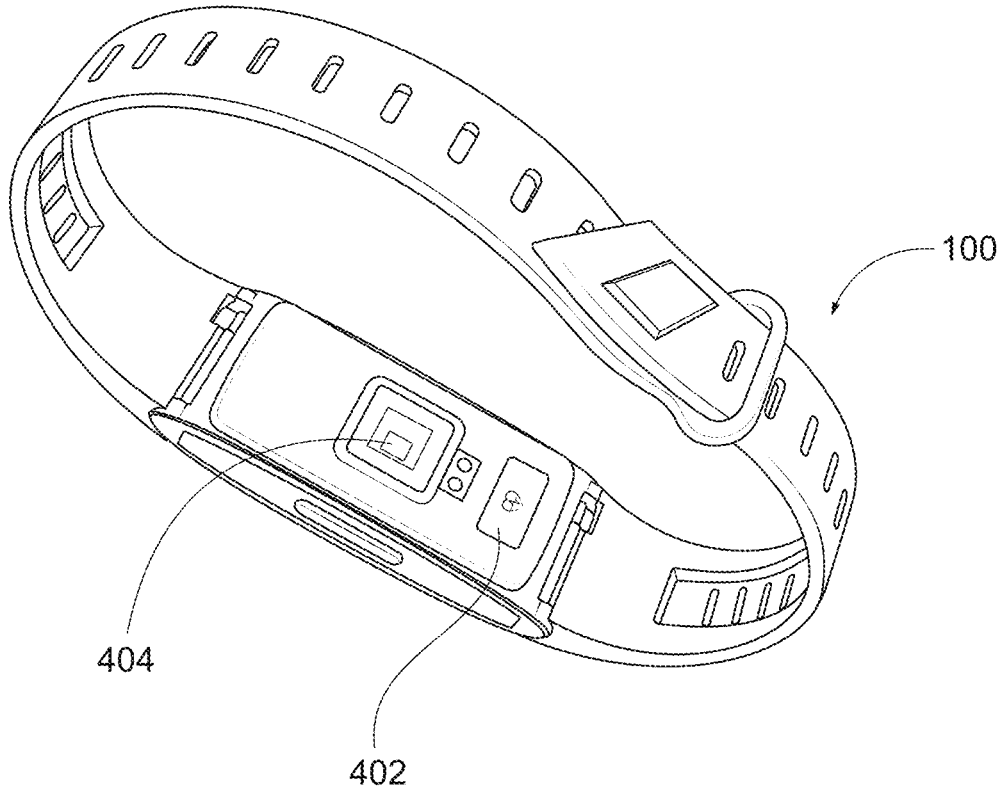
FIG. 3B is another perspective view of a personal healthcare device according to one embodiment herein.
Figure 15:
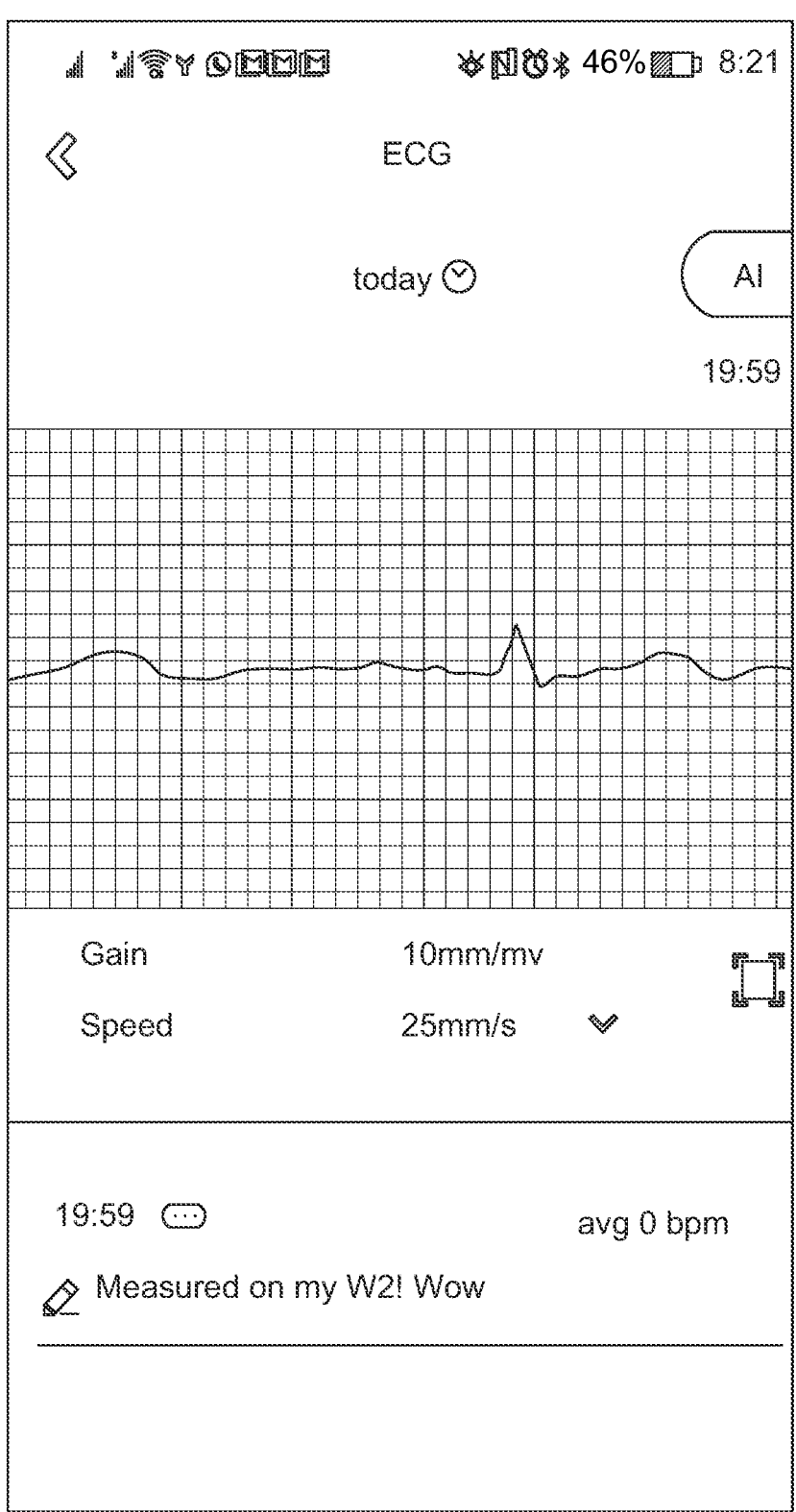

Referring to FIG. 3A, in one embodiment, the device 100 is in the form of a device that is worn on the user's wrist. In this regard, the device 100 may include a wrist band with ends that are detachably connected to each other. The device 100 may further include a mode button that when pressed for a present amount of time toggles through certain functionality. For instance, 2 seconds may turn the device 100 on, whereas 8 seconds may turn the device off. The succession of clicks may trigger other functionality, such as double select to trigger the panic button functionality. The device 100 may also include a top, outward facing face (the "outer face") containing a display 312, which may be a simple LED or something more robust such as an LCD that displays textual/numeric biometric data or a touchscreen display. In one embodiment, the device 100 includes a first sensor 308 on the outer face of the device 100 and/or a second sensor 310 on the lateral side of the device 100. The device 100 may optionally include a third sensor 309 on the outer face of the device 100, as shown. For instance, the device may include one or more bioelectric impedance sensors 308, 309. These sensors may also be on the bottom side of the device 100, as shown in FIG. 3B (402, 404). Moreover, top and bottom sensors may be used in which the user touches a top sensor 308 (and preferably 309) with one or two fingers to complete the circuit therebetween and/or with a bottom sensor 402 touching the wrist to gather additional data which enables biometric impedance to be measured and body composition to be deduced in near real-time. Fingers on sensors 308 and 309 may further detect the electrical signals produced by the user's heart to generate ECG suitable for clinical and fitness applications, as shown in FIG. 15.

Referring to FIGS. 4A and 4B, in another embodiment, the device 100 includes electrical contact sensors 308 and 309 on the top face and sensor 310 on the lateral side of the device 100. More specifically, the electrical contact sensors 308 and 309 are located on the case as the bezel, surrounding the crystal. Additionally, the sensors are electrically separated by the case, as shown. Preferably the first electrical sensor 308 is located at the top end of the watch face or crystal and the second electrical sensor 309 is located at the bottom end of the watch face or crystal. In this preferred embodiment, the user may access the functionality associated with these sensors by placing the index finger on the bezel at the top and thumb on the bezel at the bottom of the face of the watch. The sensors 308 and 308 may make up the entirety of the bezel, except for the spacers 311 that electrically separate the sensors, also as shown. The sensors 308, 309 may each form a U shape that each convers approximately half or an equal amount of the bezel of the watch and may each provide the structure for the crystal to be recessed into the case and/or the bezel.

Figure 4C:
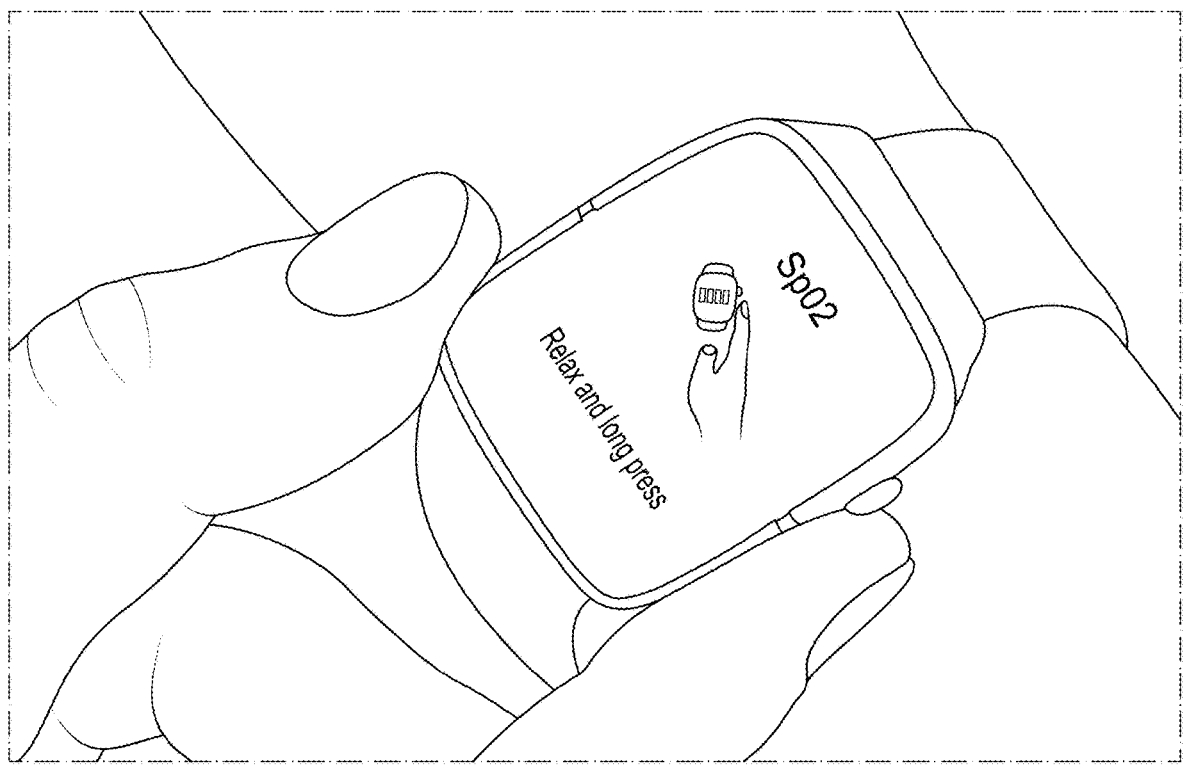
FIG. 4C is a perspective view of a personal healthcare device in operation according to one embodiment herein.

Sensor 310 is preferably located within a ridge 314 extending outward from the lateral side of the device and preferably around the perimeter of the sensor 310 such that sensor 310 is recessed within a volume created with the raised ridge 314. The sensor 310 may be covered with a transparent material recessed within or flush with the ridge 314. The case further includes an upwardly facing surface 313 for that receives the bezel sensors 308, 309, along with spacers 311. Referring to FIG. 4C, lateral sensors may be used in which the user fingertip forms a good seal with sensor 310 via the ridge 314 and from which and IR and NIR light is emitted and detected to produce a PPG signal from which SpO2 is deduced in real-time as shown in FIG. 4C. BP can be deduced by repeating a similar process. These higher quality measurements deduced from sensor 310 can be remotely compared to the PPG signal deduced measurements from the rear continually measuring sensors 404, by the server computers 106. Any discrepancies can be used to correlate and inform the machine learning process to improve the measurements deduced by sensors 404. The device 100 may further include a sensor/emitter pair, preferably inline, on the lateral side or the rear of the device 100, arranged to reflect signals between each other as with the other inline sensor/emitter embodiments discussed herein.

Figure 5:
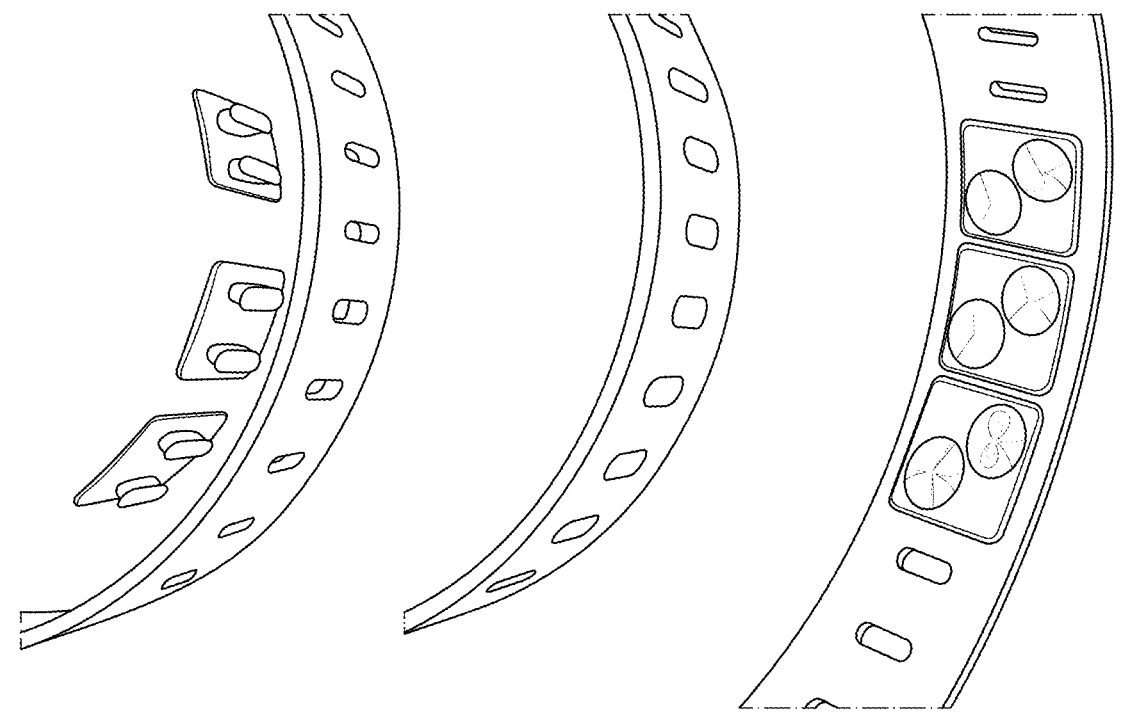
FIG. 5 are a set of views of the wrist band for a personal healthcare device according to one embodiment herein.

Finally, the device 100 may include a unique mechanism for attaching stones 304 directed to the wearer's skin. The stones are preferably installed on modular platforms that allow them to be interchangeably added to the wristband of the device, as shown in FIG. 5.

Figure 6A:
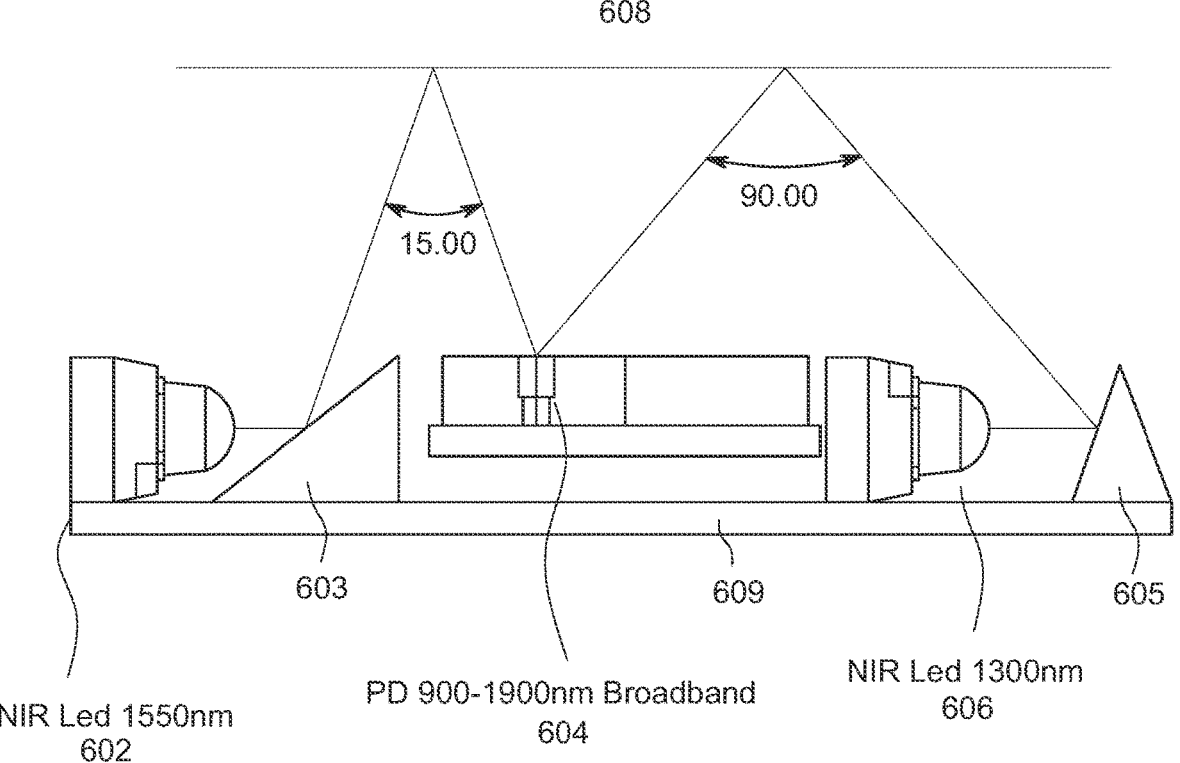
FIG. 6A is a diagram of a flat inline sensor (FIS) for a personal healthcare device according to one embodiment herein.

Referring to FIG. 6A, according to another embodiment the sensors 310 and 404 may be a flat inline sensor (FIS) 600 that may be used to obtain biometric data via the photoplethysmography (PPG) signals, such as heart rate, respiratory rate, ECG/EKG, blood pressure, glucose levels, blood alcohol, blood oxygen, etc. The FIS may be mechanically applied adjacent to the body at the surface of the skin 608, below which there are blood vessels. By applying the FIS adjacent to the body at the surface of the skin, it is possible to obtain valid PPG signals at different frequencies, which can be used to determine or otherwise derive blood glucose levels in these blood vessels.

In a preferred embodiment, the measurement of blood glucose levels is measured at the underside of the wrist, fingertip, or other surface sufficiently flat, with good access to capillaries or veins, for the FIS to register a low noise PPG signal.

In a preferred embodiment, the sensor package FIS 600 is directly connected to the main board of the device for acquisition and processing of the PPG signals.

In a preferred embodiment, the FIS may be a Surface Mounted Device (SMD) Package type having a plurality of Near Field Infrared (NIR) LEDs, 602 and 606 and a photodiode (PD) 604, the LEDs and PD mounted to the base 609 of the SMD Package, such that the PD is disposed on the FIS and/or SMD between the LEDs. In a preferred embodiment, the SMD Package may include one NIR LED with a wavelength of about 1300 nanometers (nm) (606), one NIR LED with a wavelength of about 1550 nm (602) and one Photodiode (PD) with broad range wavelength sensitivity between about 900 nm and about 1700 nm (604). It is understood that the order and/or location of the LEDs may vary. Accordingly, the inline SMD package is an exemplary embodiment and therefore not limiting. The term "about" is used herein to reflect applicable tolerances in the manufacture of such diodes.

In another embodiment, the SMD Package may include one LED with a wavelength range of about 1300 nm±10%, 606, one LED with a wavelength of about 1550 nm±10%, 602, and one PD with a broad range wavelength sensitivity between about 900 nm to about 1700 nm±10%, 604.

In operation, the user of the device 100, or his or her caregiver or authorized third party may initiate measurement directly on the menu of the device via the touchscreen display or on a menu of a connected device in communication with the device 100. The user will place his or her fingertip on sensor 310 for few seconds (usually from 30 to 60 seconds) until a light is emitted, as shown in FIG. 4C. The flow for the side sensor operation may, in certain embodiments, include selecting the desired function on the device or a connected device, placing a fingertip on the side sensor, holding the fingertip on the sensor for the necessary amount of time, view the results on the display of the device, and sync the results, e.g. via Bluetooth, IoT, etc., with the connected device (app) and/or the cloud platform that supports the remote monitoring functions of the device. The user can perform as many measurements as desired and will not need to carry or apply any external device to the fingertips. The device 100 can continue to perform all its other functions and run its applications, offering the user all the advantages of a fingertip device, without restriction or introducing any compromise to the performance or quality of measurement. The sequence of steps to initiate a side sensor measurement, from the initiation of measurement to the output of results, may be identical or similar to those steps performed by a traditional fingertip pulse oximeter, but are not necessarily so constrained.

The various sensors on the device may work together to provide more robust results. For example, to take an SpO2 measurement, the NIR and IR LEDs may be active at the same time to generate overlapping PPGs, which allow SpO2 measurements using data obtained from both the wrist and fingertip. At night, the LEDs on the back of the device, in contact with the user's wrist, may be initiated while the user is asleep for SpO2 data. The accuracy of this data may be enhanced by correlating the wrist sensor readings with SpO2 data from prior readings using the side-sensor.

The device 100 may also automatically measure certain biometric data through an internal timer. The rate at which measurements are taken may be preset or set remotely by the wearer, caregiver or an authorized third party. For example, the rate may be every 30 min, 60 min, etc., selected from a drop-down menu of available rates. The device 100 may further collect data continually, for use, for example, for inferring some of the conclusions therefrom while still displaying and charting the periodic measurements. For example, the device 100 may collect heart rate data continuously and use that to determine heart rate variability, while still only charting hourly measurements. The device 100 may further include sensors that assess biometric data on demand, i.e., when a user elects to take a measurement.

In a preferred embodiment, in operation, light from the two NIR LEDs 602, 606 is directed to the surface of the skin 608 via reflection off of two angular mirrors 603, 605, respectively, mounted to the base 609 of the SMD Package. The angle of the angular mirrors 603, 605 ensures that the light reflecting back is at a predetermined angle as shown by example in FIG. 6A, when it is then captured by PD 604. Specifically, light from LED 602 is reflected from the skin surface 608 at an angle of about 45 degrees, and light from LED 606 is reflected from the skin surface at an angle of about 90 degrees, each of the light rays captured by PD 604. In another embodiment, the range of the angle of reflection may be ±10%.

In a preferred embodiment, the sensors 310 and 404 are covered with a specially designed glass, e.g., having a thickness and curvature (or lack thereof (i.e., planar)), which correctly directs the LED light to the fingertip and the PD receives the signal from the reflected changes of light absorption in oxygenated or deoxygenated blood. As can be seen, the sensors 308 and 404 may be disposed side-by-side or in-line with each other.

As can be seen in FIG. 6A, rather than the emitter/LED oriented outward, mirrors and/or prisms can be used to reflect the signal/light emitted from the emitter/LED, which is then reflected off of the subject's skin into the receiver/sensor/PD, as the case may be. This arrangement allows for a more compact design and may allow the emitters/LEDs to be split and used for multiple purposes and receivers/sensors/PDs.

Using PPG techniques and two specific NIR LEDs at very high frequency wavelength (about 1300 and about 1550 nm) in a specific configuration, high frequency wavelength light is reflected at specific angles when it is reflected off blood glucose molecules. e.g., 90 degrees for 1550 nm wavelength light and 45 degrees for the 1300 nm wavelength light.

FIG. 6B outlines the details of exemplary LEDs that may be used in a preferred embodiment of the FIS. For example, the exemplary LEDs are of wavelengths of about 640 nm, about 940 nm, about 1300 nm, and about 1550 nm. For detection and monitoring of heart rate, the combination of LEDs of wavelengths about 640 nm, about 940 nm, about 1300 nm, and about 1550 nm may be used. For detection and monitoring of blood oxygen, the combination of LEDs of wavelengths about 640 nm and about 940 nm may be used. For detection and monitoring of blood glucose, the combination of LEDs of wavelengths 640 nm, 940 nm, 1300 nm, and 1550 nm may be used.

FIG. 6C outlines details of exemplary photodiodes and photodiode combinations that may be used according to a preferred embodiment of the FIS.

Figure 6D:
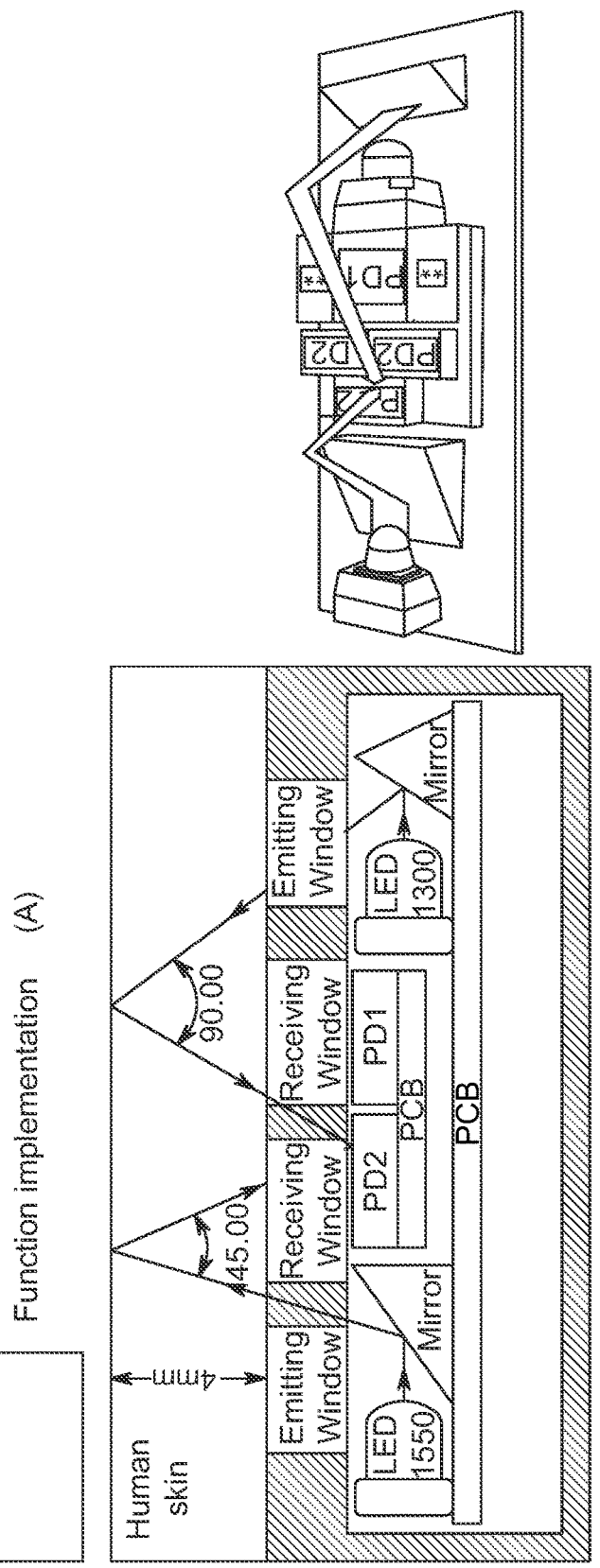
FIG. 6D is a diagram showing a functional implementation of the FIS adjacent to skin according to one embodiment herein.

FIG. 6D displays functional implementation of the FIS adjacent to the skin for LED 1300 and LED 1550 as the light is reflected at a depth of some 4 mm below the skin. The angle between 602 and 604 is 45 degrees and the wider angle between 606 and 604 is 90 degrees.

Figure 6E:
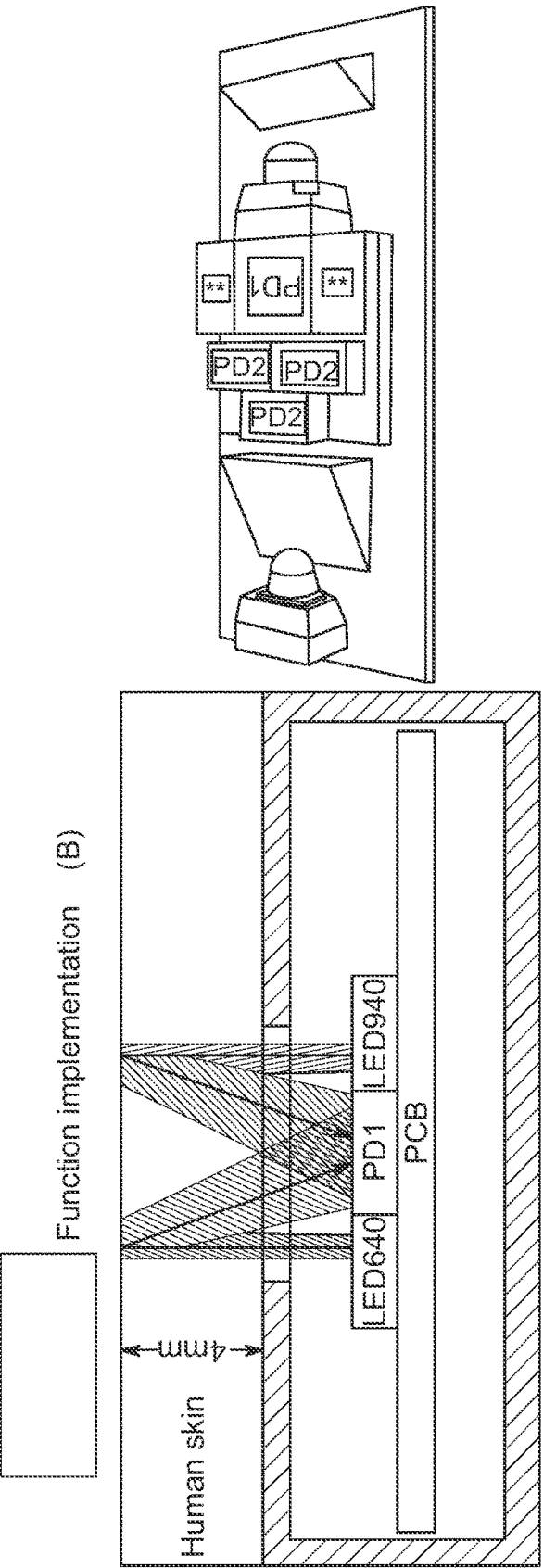
FIG. 6E is another diagram showing a functional implementation of the FIS adjacent to skin according to one embodiment herein
Figure 6E:
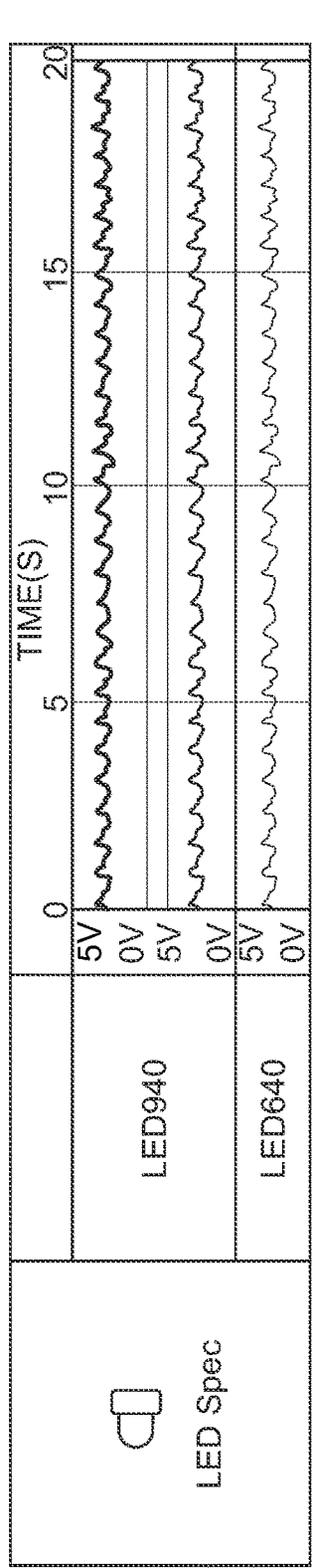

FIG. 6E displays the functional implementation of the FIS adjacent to the skin for LED940 and LED640 as the light is reflected at a depth of some 4 mm below the skin.

Referring back to FIG. 3B, the bottom or underside of the device 100 is shown. This side may include one or more sensors thereon in or around sensor 402. The bottom of the device 100 preferably includes a plurality of sensors, including at least a synchronous red light and near infrared light emitters/sensors.

Referring to FIG. 5, the details of the wristband are shown. Specifically, the band includes a plurality of apertures, equally spaced to accommodate the pedestals having stones thereon. The cross section of the apertures is preferably hourglass shaped to retain similarly shaped legs on the pedestal. The pedestals are inserted from the inside of the band through the apertures therein. The pair of legs of the pedestals fit flush with the outside of the band, as shown. The tops of the pedestals include therein at least one stone. A stone is generally a material that is believed to have beneficial properties, such as gold, silver, copper, germanium, magnets, salt, etc. The pedestals beneficially bring the stones into contact with the wearer's skin.

Figure 7:
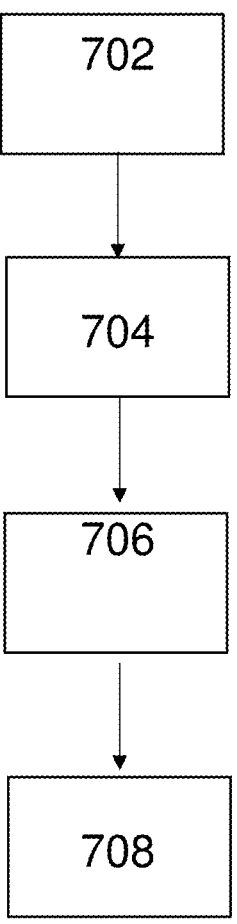
FIG. 7 is a flowchart of a method for training a learning machine to interpret data from a personal healthcare device according to one embodiment herein.

FIG. 7 presents a flowchart of a method for training a learning machine to interpret data from a personal healthcare device according to one embodiment herein according to one embodiment herein. In at least one embodiment, the device 100 employs synchronous red light and near infrared light to generate a photoplethysmograph (PPG) signal that is analyzed to determine a biometric measure, such as blood glucose level (BGL) or any of the other biometrics discussed herein. A PPG signal is received by an analytical server from the device 100, step 702. The steps in assessing biometrics using PPG may be premised on the correlation between PPG and BGL, blood pressure, etc. Similarly, the correlation between PPG and key nutrition elements and/or blood vessel endothelium health status may also be analyzed.

This analysis may be achieved by sampling, for example, 1000 persons for PPG signal data, standard BGL, blood pressure, etc., to produce training data for machine learning. The test may be undertaken, for example, before breakfast every day for 14 consecutive days.

The algorithms for determining BGL and other biometrics from PPG data may be derived with the following exemplary process:

Obtaining biometric data—biometric data is received, step 704—using, for example, a personal healthcare device with a flat inline sensor with 660 nm red light and 940 nm near infrared light to get PPG data, the device may take 2 readings allowing 1 minute for each reading. Then the BGL may be tested using a medical level micro trauma blood glucose monitor. Blood pressure may also be taken with a cuff sphygmomanometer, again ensuring that two readings are taken. For each person, the test will continue for 2 weeks, 2 times every day around the same time each day with the first time in the morning before breakfast and the second time in the afternoon, 1 hour after eating lunch. A person's sex, age, height, weight, country, ethnicity, cardiovascular and cerebro-vascular diseases history, metabolism diseases history, family diseases history, continuo and any ongoing medication or history of medical conditions may be provided along with the biometric data. The location, amount of caffeine taken, smoking and if so, to what extent, emotion, fatigue and so on may also be recorded.

The PPG data generated may be processed to get the clean signal. Character vector data is extracted, step 706—the PPG signal may be filtered with a band pass filter, allowing signals of about 0.5 Hz to about 5 Hz and then an adaptive noise canceller may be applied using the recursive least squares or similar method. The key to usable data is to find the effective reference signal and extract the character vectors. From the clean signal, character vectors may be distinguished and extracted, and then supervised machine learning may be applied to compute a correlation. The resulting formula may be assessed against a subset of the test data to predict validity of the algorithm.

Exemplary PPG Character Vectors:

Kaiser-Teager power energy value: $KTE_n = x(n)^2 - x(n+1) x(n-1)'$ where x is the electromyographic value and n is the sample number, segmented real-time power energy value: $KTE_n$, mean value $KTE_n^\mu$, mean square deviation $KTE_n^\circ$, quarter distance $KTE_n^\alpha$, slewness $KTE_n^\beta$, and corresponding segments $KTE^\mu$, $KTE^\circ$, $KTE^\alpha$, $KTE^\beta$ may be obtained.

Heart rate value: from the PPG wave, the corresponding $HR^\mu$, $HR^\circ$, $HR^\alpha$, $HR^\beta$ may be computed.

Spectral entropy can be useful and to be considered, for determining the FFT (fast Fourier transform) for the segmented signal, means $X_n \leftarrow FFT(x(n), L)$, followed regularization. Knowing the probability mass function $Px''$, then the entropy may be computed, $H \leftarrow Px'' Log(Px'')$. The segmented data may be: $H_n^\mu$, $H_n^\circ$, $H_n^\alpha$, $H_n^\beta$. If computing overflow happens, conduct log function, $Log E \leftarrow Log(x(n))'$ knowing $Log E^\circ$ and $Log E^\alpha$.

Red light and near infrared light peak values, Pr, Pi may also be computed independent of the power value. To avoid the respiratory impact, the segmented time duration can be 5 s to 10 s, the signal is x(n), and the corresponding matrix is Xi. When conducting this computation, new valid vector elements may be added and trivial impact signals removed.

A correlation between PPG signal and biometric data may be determined using supervised machine learning, step 708. The vector dimension may be from 10 to 20 from the PPG data. Randomly, 90% of the data may be placed into the training set, another 10% into the test set. A machine learning algorithm can be used to compare: least square method linear recursive compute, logistic recursive compute, support vector machine (SVM), classification and regression trees (CART), random forest, neural network (NN), AdaBoost, and so on. SVM may use SMO (Sequential Minimal Optimization) and kernel function, using the radial basis function as kernel function. The NN may be BP (back propagation) and Hopfield to do the test. Based on the training and testing via machine learning, certain aspects of the biometric data may be correlated with certain PPG waves.

Figure 14:
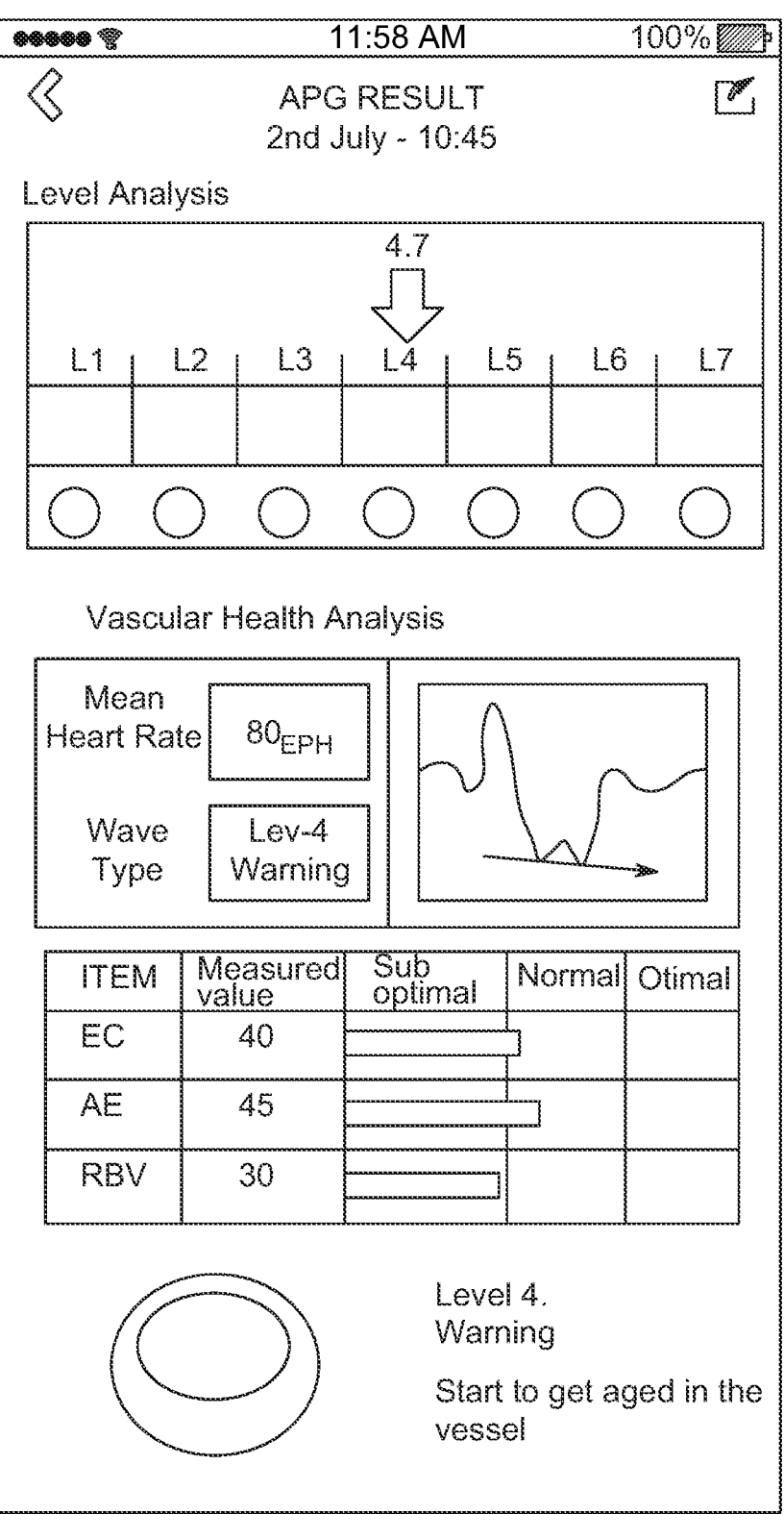

The device's high-quality photoplethysmogram (PPG) obtained using the side sensor 310 illuminates the fingertip and measures changes in light absorption due to blood volume changes in the microvascular bed of tissue. The second derivative of this PPG can be used to determine vascular aging and the degree of atherosclerosis, which can be presented on a 1-7 scale on your interface screen, as shown in FIG. 14.

Figure 8:
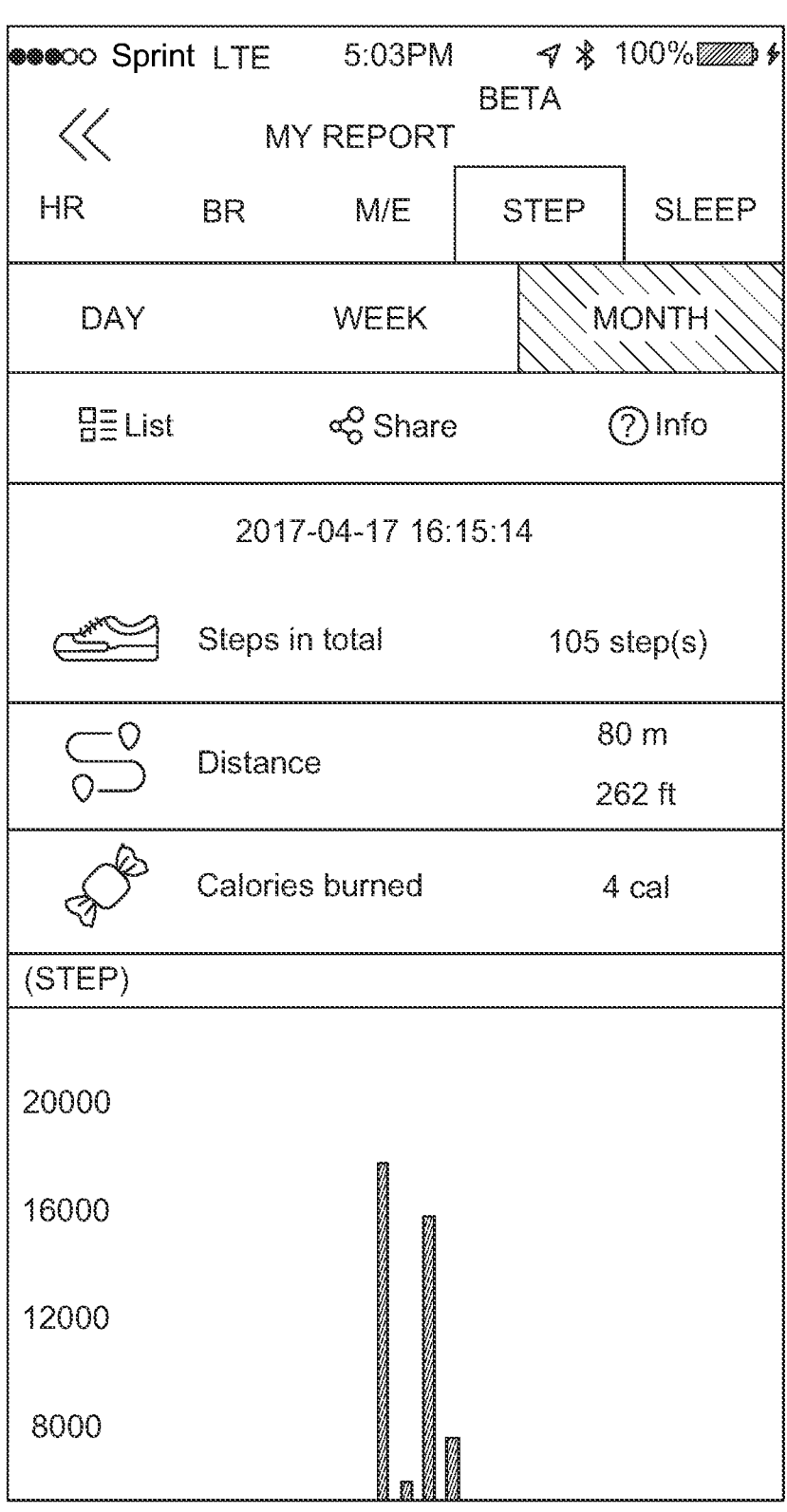
FIGS. 8-15 are a set of interface screens displayed on a mobile device app associated with the personal healthcare device according to one embodiment herein.

FIG. 8 presents an interface screen for displaying step data of a user that is determined from a personal healthcare device according to one embodiment herein. The interface may include step data according to a daily, weekly, or monthly basis. The personal healthcare device may record an amount of total steps, distance, and calories burned. The amount of steps may also be provided in a chart over a given period.

Figure 9A:
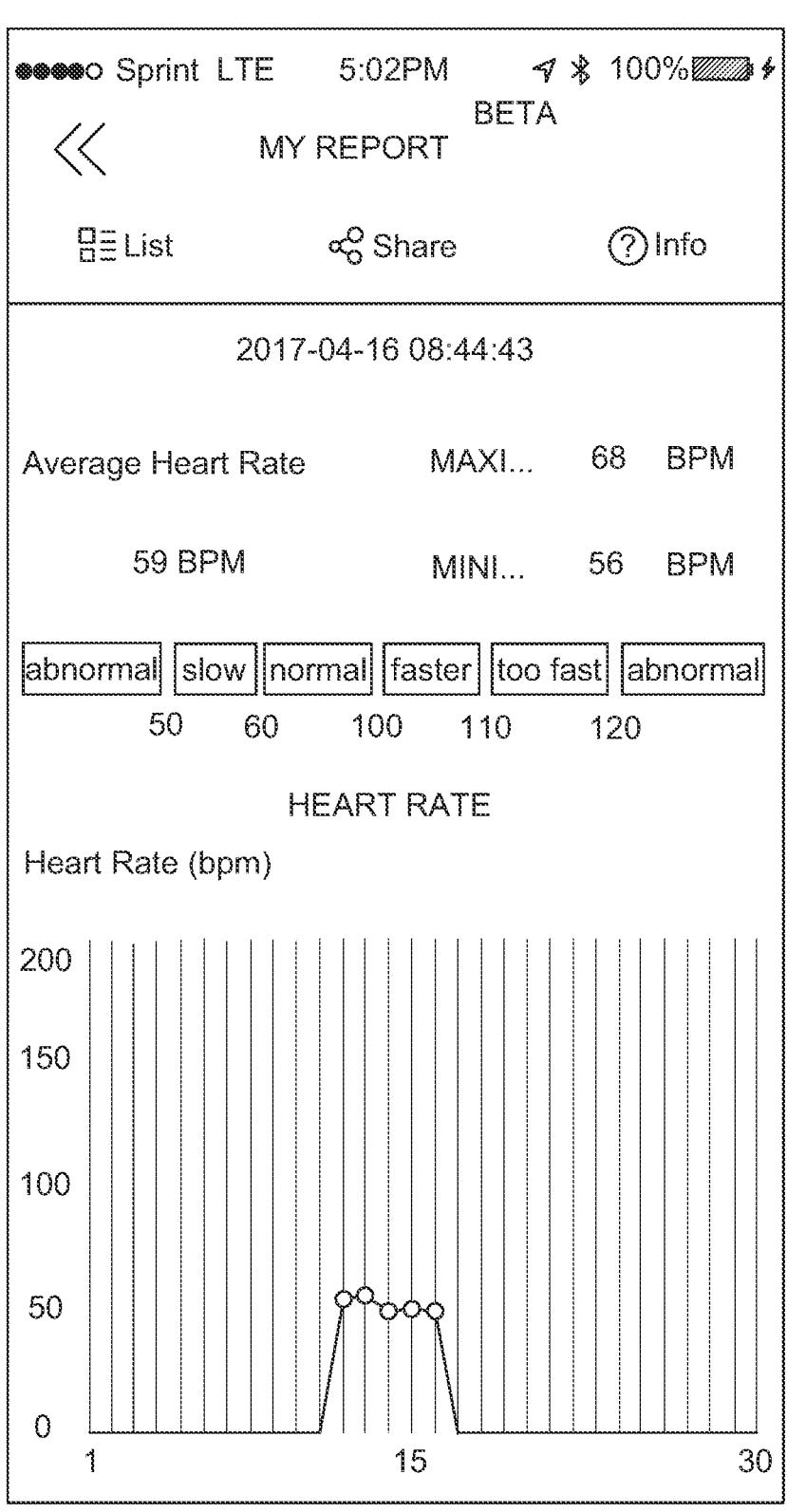
Figure 9B:
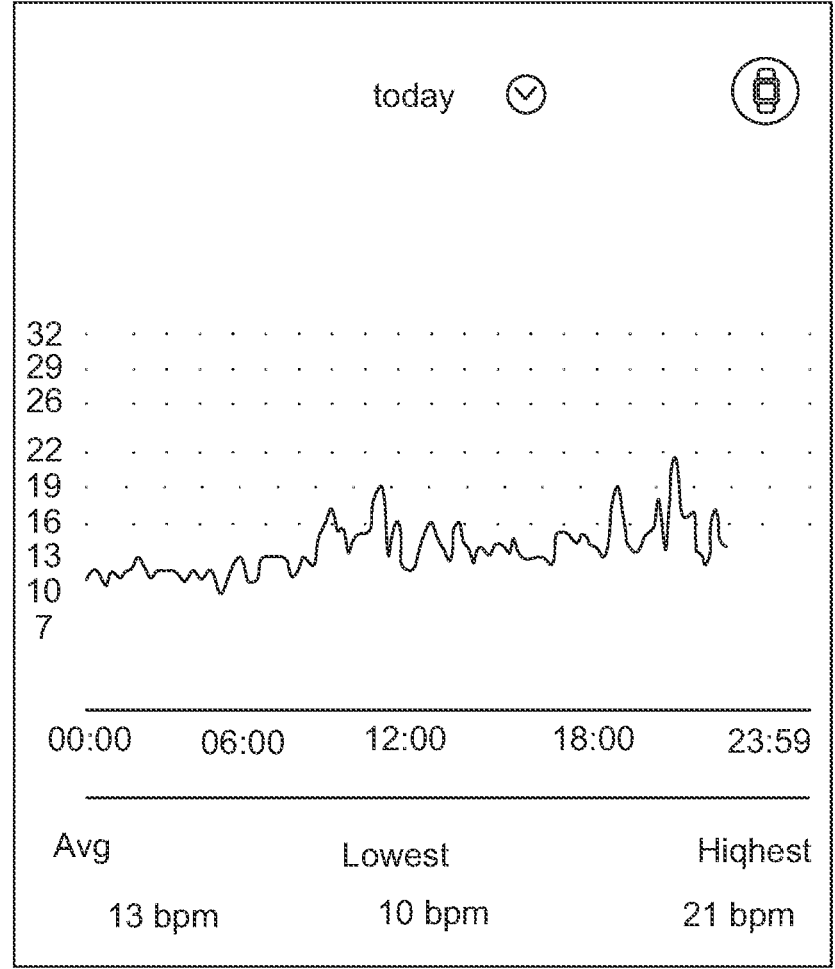

FIG. 9 presents an interface screen for displaying heart rate data of a user that is determined from a personal healthcare device according to one embodiment herein. The interface may include a record of maximum and minimum of beats per minute along with a guideline range of normal/abnormal heart rate. The heart rate interface may further calculate a user's average heart rate and chart the user's heart rate over a given period.

Figure 10:
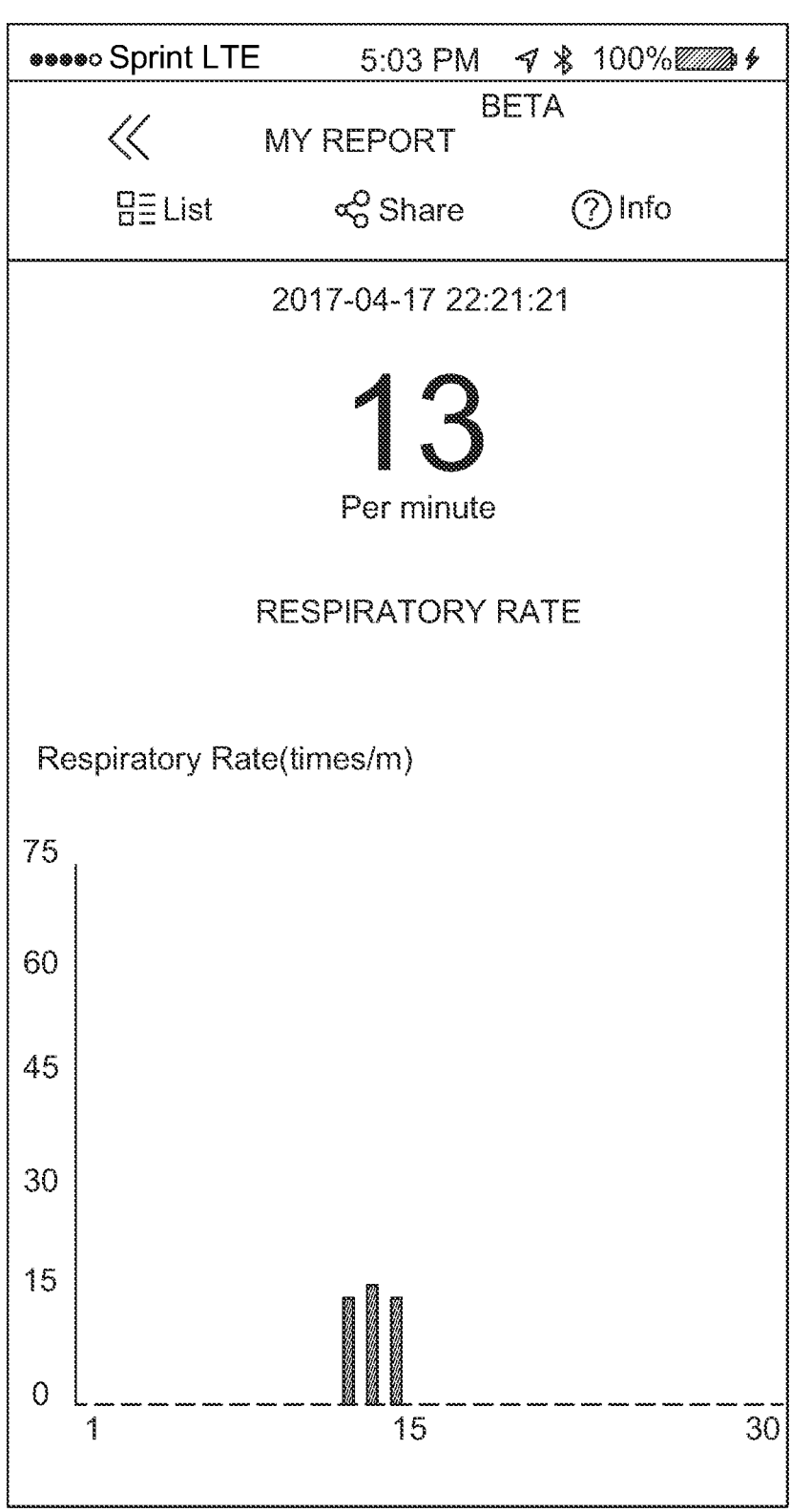

FIG. 10 presents an interface screen for displaying respiratory rate data of a user that is determined from a personal healthcare device according to one embodiment herein. The interface may present a determined respiratory rate (times per minute) for a user as determined by the personal healthcare device. The determined respiratory rate of the user may be charted over a given period.

Figure 11:
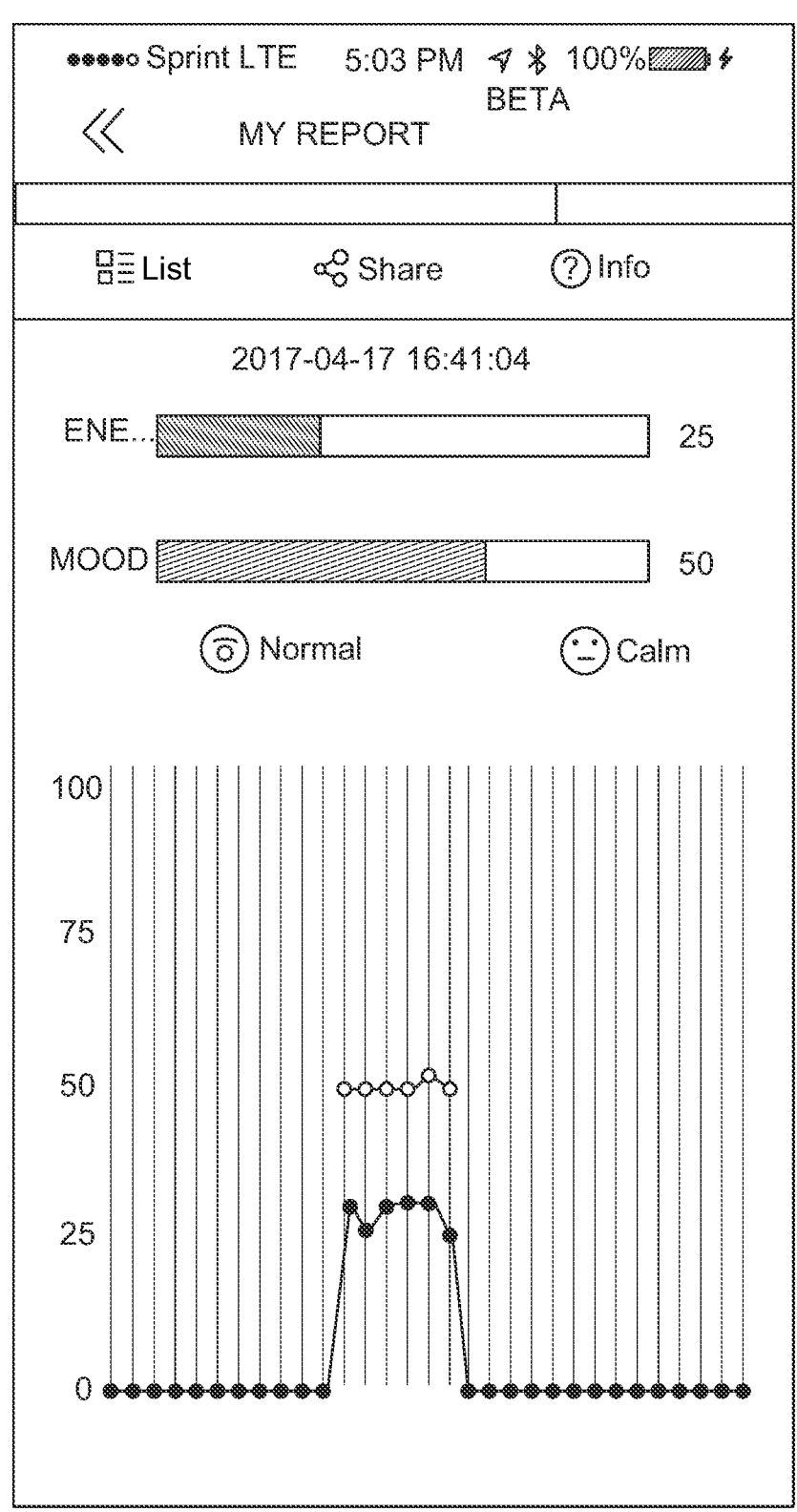

FIG. 11 presents an interface screen for displaying energy and mood data of a user that is determined from a personal healthcare device according to one embodiment herein. Energy and mood of a user may be calculated according to a predetermined scale. For example, an energy level of '25' may be normal and mood of '50' may indicate that the user is calm. Energy and mood may be charted over a given period.

Figure 12A:
Figure 12B:
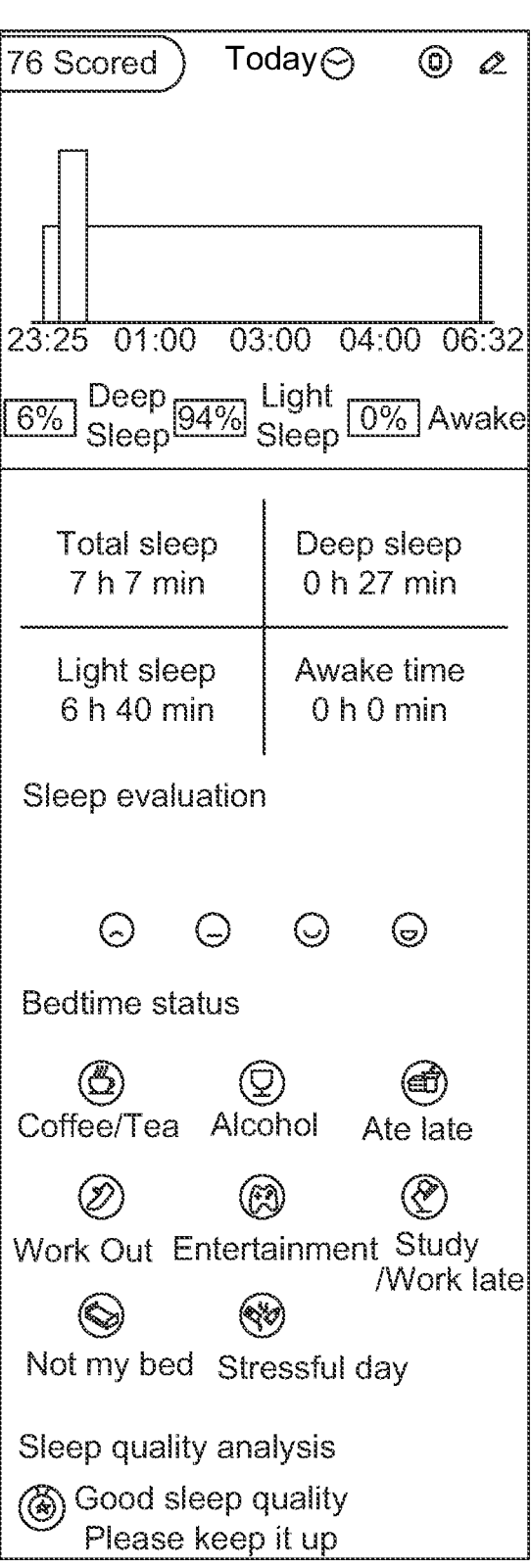

FIG. 12 presents an interface screen for displaying sleep data of a user that is determined from a personal healthcare device according to one embodiment herein. Sleep data may include total sleep duration, duration of deep sleep, duration of light sleep, and how many times during sleep did the user wake up. One or more data points for sleep may be plotted on a chart over a given period.

Figure 13:
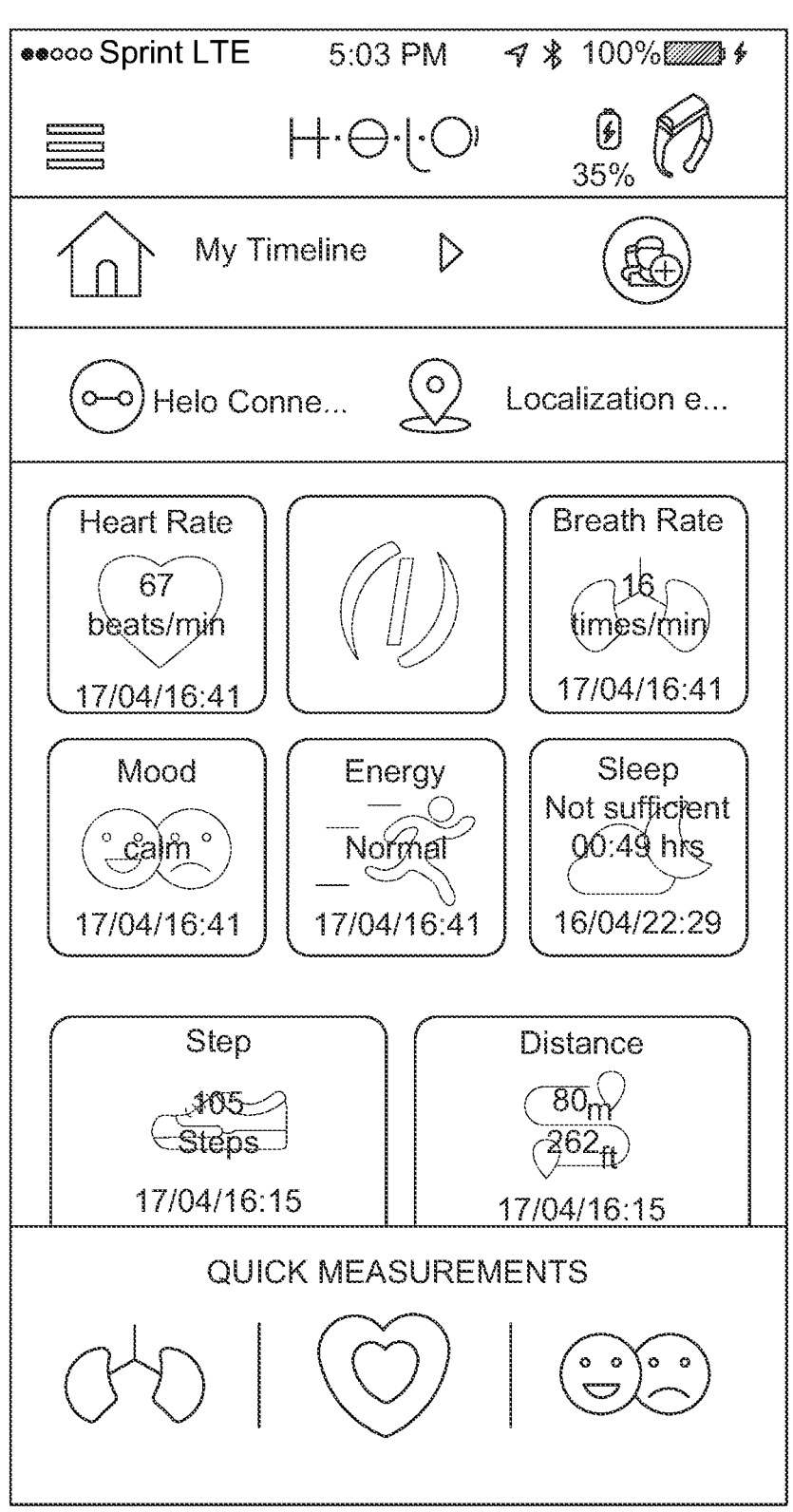

FIG. 13 presents an exemplary home screen of a personal healthcare device according to one embodiment herein. The home screen may include a quick summary of the data described with respect to FIGS. 8-12. Each data category may be presented in selectable tiles that can be expanded to display the data in detail. Additionally, the home screen may provide a feature to take "quick measurements" of respiratory rate, heart rate, energy and mood, for example.

While the foregoing invention has been described in some detail for purposes of clarity and understanding, it will be appreciated by one skilled in the art, from a reading of the disclosure, that various changes in form and detail can be made without departing from the true scope of the invention.

What is claimed is:

1. A method, in a data processing system comprising a processor and a memory, for measuring personal health, the method comprising:

detecting a plurality of photoplethysmograph (PPG) waves by a personal healthcare device, the plurality of PPG waves are generated by infra-red, green, or red lights emitted from the personal healthcare device, wherein the personal health care device comprises:

a bezel having a top bezel portion and a bottom bezel portion;

a top outward facing face, a lateral side, and a bottom side, wherein the bottom side faces a user's wrist; and a plurality of electrical contact sensors, wherein a first of the plurality of sensors is located at the top bezel portion and a second of the plurality of sensors is located at the bottom bezel portion wherein the first and second sensors are configured to complete a circuit therebetween when a user contacts the first sensor with a first surface of the user's skin and contacts the second sensor with the first or a second surface of the user's skin;

a lateral side sensor located within a recessed ridge on the lateral side of the personal healthcare device wherein the lateral side sensor detects an overlapping photoplethysmograph (PPG) wave, wherein the overlapping PPG wave overlaps at least one of the plurality of PPG waves;

transmitting the detected plurality of PPG waves to a server, wherein the server processes the detected plurality of PPG waves and infers therefrom biometric data based on machine learned correlations generated from a training set of PPG waves and biometric data;

receiving the biometric data from the server; and generating an interface screen comprising the biometric data.

2. The method of claim 1, wherein the personal health care device further comprises:

an inline sensor (IS) comprising a first Near Field Infrared (NIR) Light Emitting Diode (LED), a second NIR LED, and a photodiode with wavelength sensitivity range between about 900 nm to about 1700 nm±10%, the photodiode located on the IS between the first and second NIR LEDs and configured relative thereto to receive reflected light from the first and second NIR LEDs, and a first and second angular mirror, each configured to reflect light from either of the first and second NIR LEDs onto a user's skin and for the user's skin to reflect light back to the photodiode, wherein the personal healthcare device generates the detected PPG wave based on the light reflected off of the user's skin.

3. The method of claim 2, wherein the first NIR LED has a first wavelength in the near infrared spectrum and the second NIR LED has a second wavelength in the near infrared spectrum.

4. The method of claim 1, wherein a first intermediate detected PPG wave is generated from light reflected off of the user's skin from the first NIR LED and a second intermediate detected PPG wave is generated from light reflected off of the user's skin from the second NIR LED, and the detected PPG wave is generated from the combination of the first and second intermediate detected PPG waves.

5. The method of claim 1, wherein the first NIR LED has a wavelength of about 1550 nm±10% and the second NIR LED has a wavelength of about 1300 nm±10%.

6. The method of claim 1, wherein light from the first NIR LED is directed to the user's skin via the first angular mirror, and light from the second NIR LED is directed to the user's skin via the second angular mirror, such that the light from the first NIR LED is reflected back off of blood glucose molecules to the photodiode at a first predetermined angle and light from the second NIR LED is reflected back off of blood glucose molecules to the photodiode at a second predetermined angle.

7. The method of claim 6, wherein the first predetermined angle is about 45 degrees and the second predetermined angle is about 90 degrees.

8. The method of claim 1 wherein the lateral side sensor is recessed within the recessed ridge extending outward from the lateral side of the device, wherein the recessed ridge is configured to form a seal with the first or second surface of the user's skin when the user contacts the at least one of the plurality of sensors with the first or second surface of the user's skin.

9. The wearable device of claim 2 wherein the plurality of sensors are covered with a glass configured to direct light from either of the first and second NIR LEDs onto a user's skin and receive reflected light from the first and second NIR LEDs at the photodiode.

10. The method of claim 2, wherein the inline sensor further comprises a PCB, and the first and second NIR LEDs, photodiode, and first and second angular mirrors are each attached to the PCB.

11. The method of claim 10, wherein the first and second NIR LEDs are configured to emit light in a direction parallel to the PCB, and wherein the mirrors reflect the emitted light at an oblique angle relative to the PCB.

12. The method of claim 1, wherein the biometric data comprises blood glucose levels.

13. The method of claim 1, wherein the server processes the PPG wave and infers therefrom biometric statistics and wherein the biometric statistics comprise at least one of overall health, changes in health, mood, sleep quality, fatigue, and stress.

14. The method of claim 1, wherein the machine learned correlations are based on PPG character vectors including a Kaiser-Teager power energy value, a heart rate value, and a spectral entropy value.

15. A wearable device for measuring personal health configured to detect a plurality of photoplethysmograph (PPG) waves photoplethysmograph (PPG) wave generated by infra-red, green, or red lights emitted from the personal healthcare device, the device comprising:

a bezel having a top bezel portion and a bottom bezel portion;

a top outward facing face, a lateral side, and a bottom side, wherein the bottom side faces a user's skin;

a plurality of electrical contact sensors, wherein a first of the plurality of sensors is located at the top bezel portion and a second of the plurality of sensors is located at the bottom bezel portion wherein the first and second sensors are configured to complete a circuit therebetween when a user contacts the first sensor with a first surface of the user's skin and contacts the second sensor with the first or a second surface of the user's skin;

a lateral side sensor located within a recessed ridge on the lateral side of the personal healthcare device wherein the lateral side sensor detects an overlapping photoplethysmograph (PPG) wave, wherein the overlapping PPG wave overlaps at least one of the plurality of PPG waves;

a network communication module configured to transmit the detected plurality of PPG waves to a server, wherein the server processes the detected plurality of PPG waves and infers therefrom biometric data based on machine learned correlations generated from a training set of PPG waves and biometric data;

a processor configured to generate the biometric data; and an interface screen comprising the biometric data.

16. The wearable device of claim 15, further comprising:

an inline sensor (IS) comprising a first Near Field Infrared (NIR) Light Emitting Diode (LED), a second NIR LED, and a photodiode with wavelength sensitivity range between about 900 nm to 1700 nm±10%, the photodiode located on the IS between the first and second NIR LEDs and configured relative thereto to receive reflected light from the first and second NIR LEDs; and a first and second angular mirror, each configured to reflect light from either of the first and second NIR LEDs onto a user's skin and for the user's skin to reflect light back to the photodiode, wherein the personal healthcare device generates the detected PPG wave based on the light reflected off of the user's skin.

17. The wearable device of claim 15, wherein the lateral side sensor is recessed within the recessed ridge extending outward from the lateral side of the device, wherein the recessed ridge is configured to form a seal with the first or second surface of the user's skin when the user contacts the at least one of the plurality of sensors with the first or second surface of skin.

18. The wearable device of claim 16, wherein the plurality of sensors are covered with a glass configured to direct light from either of the first and second NIR LEDs onto a user's skin and receive reflected light from the first and second NIR LEDs at the photodiode.

19. The wearable device of claim 15 wherein the server processes the PPG wave and infers therefrom biometric statistics and wherein the biometric statistics comprise at least one of overall health, changes in health, mood, sleep quality, fatigue, and stress.

20. The wearable device of claim 15, wherein the machine learned correlations are based on PPG character vectors including a Kaiser-Teager power energy value, heart rate value, and spectral entropy value.

* * * * *